US012793860B2

(12) United States Patent
Gharpure et al.

(10) Patent No.: US 12,793,860 B2
(45) **Date of Patent: *Nov. 10, 2026**

(54) PROVIDING MEDICAL INSIGHTS TO A DOCTOR ENGAGED IN A CONVERSATION WITH A PATIENT BASED ON A CONSENSUS OF MUTLIPLE ARTIFICIAL INTELLIGENCE (AI) SPECIALISTS

(71) Applicant: ODIGGO, INC., Santa Clara, CA (US)

(72) Inventors: Chaitanya Gharpure, Santa Clara, CA (US); Ahmed Omar, Santa Clara, CA (US); Henry Duong, Santa Clara, CA (US); Amit Srirang Kumthekar, Santa Rosa, CA (US); Zion David Tilley, Katy, TX (US); Michael Magnoli, Vernon, CT (US)

(73) Assignee: ODIGGO, INC., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/368,376

(22) Filed: Oct. 24, 2025

(65) Prior Publication Data

US 2026/0066138 A1 Mar. 5, 2026

Related U.S. Application Data

(63) Continuation of application No. 19/253,887, filed on Jun. 29, 2025, now Pat. No. 12,525,363, which is a (Continued)

(51) Int. Cl.
*G16H 80/00* (2018.01)
*G16H 50/20* (2018.01)

(52) U.S. Cl.
CPC ............ *G16H 80/00* (2018.01); *G16H 50/20* (2018.01)

(58) Field of Classification Search
CPC ........ G16H 80/00; G16H 50/20; G16H 10/20; G10L 15/32; G10L 15/183
See application file for complete search history.

(56) References Cited

U.S. PATENT DOCUMENTS 12,008,332 B1 * 6/2024 Gardner .................. G06F 40/56
2020/0258510 A1 * 8/2020 Lavery ................... G16H 10/20
(Continued)

FOREIGN PATENT DOCUMENTS

WO WO-2019016647 A1 * 1/2019 ............ G16H 70/00

OTHER PUBLICATIONS

Treder et al., Introduction to Large Language Models (LLMs) for dementia care and research, May 14, 2024, Frontiers in Dementia, pp. 1-30. (Year: 2024).*

*Primary Examiner* — Christopher L Gilligan
(74) *Attorney, Agent, or Firm* — Shiv S. Naimpally; FP; Sikander M. Khan

(57) ABSTRACT

In some aspects, a triage artificial intelligence (AI) continually receives a portion of a conversation between a doctor and a patient. When the triage AI determines that the conversation includes a first set of trigger words of a first symptom, the triage AI selects a first AI specialist in a first medical specialty from a plurality of AI specialists and provides it access to the conversation. When the triage AI determines that the conversation includes a second set of trigger words of a second symptom, the triage AI selects a second AI specialist in a second medical specialty from the plurality of AI specialists and provides it access to the conversation. The consensus AI determines a consensus answer to questions sent to a subset of the plurality of AI specialists and provides the consensus answer to a continually updated user interface of a computing device associated with the doctor.

20 Claims, 10 Drawing Sheets

Related U.S. Application Data continuation-in-part of application No. 18/902,532, filed on Sep. 30, 2024, now Pat. No. 12,347,573, which is a continuation-in-part of application No. 18/823,175, filed on Sep. 3, 2024, now Pat. No. 12,254,966.

(56) References Cited

U.S. PATENT DOCUMENTS

| | | | | |
|---|---|---|---|---|
| 2024/0347202 | A1* | 10/2024 | Nelson | G16H 50/20 |
| 2024/0363246 | A1* | 10/2024 | Ganesan | G16H 10/60 |
| 2025/0140404 | A1* | 5/2025 | Dua | G16H 50/20 |

* cited by examiner

PROVIDING MEDICAL INSIGHTS TO A DOCTOR ENGAGED IN A CONVERSATION WITH A PATIENT BASED ON A CONSENSUS OF MUTLIPLE ARTIFICIAL INTELLIGENCE (AI) SPECIALISTS

The present non-provisional patent application claims priority from U.S. Non-Provisional application Ser. No. 19/253,887 filed on Jun. 29, 2025 which is incorporated herein by reference in its entirety and for all purposes as if completely and fully set forth herein

BACKGROUND

Field of the Technology

The technology disclosed relates to artificial intelligence type computers and digital data processing systems and corresponding data processing methods and products for emulation of intelligence (i.e., knowledge-based systems, reasoning systems, and knowledge acquisition systems); and including systems for reasoning with uncertainty (e.g., fuzzy logic systems), adaptive systems, machine learning systems, and artificial neural networks. In particular, the technology disclosed relates generally to systems and techniques to use multiple artificial intelligence (AI) specialists to provide insights to a doctor while the doctor is engaged in conversation with a patient.

Description of the Related Art

Currently, when a patient visits a doctor, the doctor has a conversation with the patient in which the doctor asks questions and the patient provides responses. Given the vast number of ailments that can present similar symptoms, the doctor may, in some cases, not ask particular questions and/or request particular follow-up actions (e.g., lab tests, referral to a specialist, or the like) related to possible ailments. In such cases, the doctor may call the patient or ask the patient to come in for a second visit to ask the particular questions. Such a process is time consuming and may potentially delay the patient from receiving the appropriate treatment.

In addition, a doctor, such as a general practitioner (GP), may determine that the patient has symptoms that require the patient to see a specialist, such as, for example, a cardiologist (for heart-related issues), a pulmonologist (for respiratory issues), an endocrinologist (for endocrine-related issues), and the like. In such cases, referring the patient to one or more specialists may result in a delay in treating the patient's symptoms.

SUMMARY OF THE TECHNOLOGY DISCLOSED

This Summary provides a simplified form of concepts that are further described below in the Detailed Description. This Summary is not intended to identify key or essential features and should therefore not be used for determining or limiting the scope of the claimed subject matter.

In some aspects, a triage artificial intelligence continually receives a portion of a conversation between a doctor and a patient. The triage artificial intelligence comprises a large language model that has been trained using training data that includes multiple audio conversations between doctors and patients. When the triage artificial intelligence determines that the conversation includes a first set of trigger words associated with a first symptom of the patient, the triage artificial intelligence (1) selects, based on the first set of trigger words associated with the first symptom, a first artificial intelligence specialist in a first medical specialty from a plurality of artificial intelligence specialists and (2) provides the first artificial intelligence specialist with access to the conversation between the doctor and the patient. When the triage artificial intelligence determines that the conversation includes a second set of trigger words associated with a second symptom of the patient, the triage artificial intelligence selects, based on the second set of trigger words associated with the second symptom, a second artificial intelligence specialist in a second medical specialty from the plurality of artificial intelligence specialists and provides the second artificial intelligence specialist with access to the conversation between the doctor and the patient. The consensus artificial intelligence determines a consensus answer to a set of questions sent to a subset of the plurality of artificial intelligence specialists that includes the first artificial intelligence specialist and the second artificial intelligence specialist and provides the consensus answer to a continually updated graphical user interface of a computing device associated with the doctor. The consensus answer is displayed using a text-based presentation that has a different graphical presentation than other information displayed by the graphical use interface. The triage artificial intelligence is retrained using at least the conversation between the doctor and the patient.

BRIEF DESCRIPTION OF THE DRAWINGS

A more complete understanding of the present disclosure may be obtained by reference to the following Detailed Description when taken in conjunction with the accompanying Drawings. In the figures, the left-most digit(s) of a reference number identifies the figure in which the reference number first appears. The same reference numbers in different figures indicate similar or identical items.

DETAILED DESCRIPTION

Figure 1:
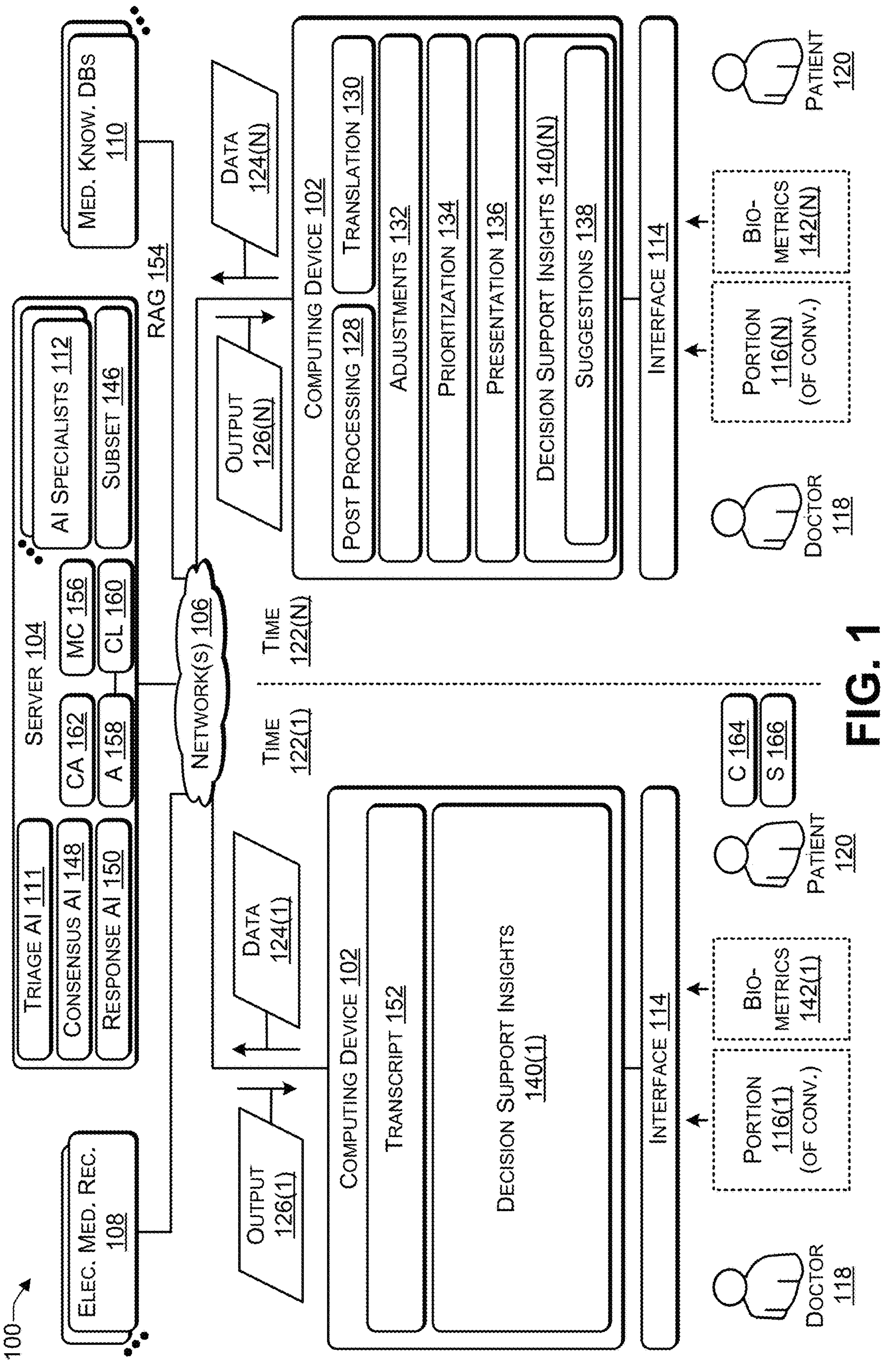
FIG. 1 is a block diagram of a system illustrating multiple artificial intelligence (AI) receiving portions of a conversation between a doctor and a patient and generating decision support insights for the doctor, according to some implementations.

The technology disclosed can be practiced as a system, method, or article of manufacture. One or more features of an implementation can be combined with the base implementation. Implementations that are not mutually exclusive are taught to be combinable. One or more features of an implementation can be combined with other implementations. This disclosure periodically reminds the user of these options. Omission from some implementations of recitations that repeat these options should not be taken as limiting the combinations taught in the preceding sections—these recitations are hereby incorporated forward by reference into each of the following implementations.

One or more implementations and clauses of the technology disclosed, or elements thereof can be implemented in the form of a computer product, including a non-transitory computer readable storage medium with computer usable program code for performing the method steps indicated. Furthermore, one or more implementations and clauses of the technology disclosed, or elements thereof can be implemented in the form of an apparatus including a memory and at least one processor that is coupled to the memory and operative to perform exemplary method steps. Yet further, in another aspect, one or more implementations and clauses of the technology disclosed or elements thereof can be implemented in the form of means for carrying out one or more of the method steps described herein; the means can include (i) hardware module(s), (ii) software module(s) executing on one or more hardware processors, or (iii) a combination of hardware and software modules; any of (i)-(iii) implement the specific techniques set forth herein, and the software modules are stored in a computer readable storage medium (or multiple such media).

The clauses described in this section can be combined as features. In the interest of conciseness, the combinations of features are not individually enumerated and are not repeated with each base set of features. The reader will understand how features identified in the clauses described in this section can readily be combined with sets of base features identified as implementations in other sections of this application. These clauses are not meant to be mutually exclusive, exhaustive, or restrictive; and the technology disclosed is not limited to these clauses but rather encompasses all possible combinations, modifications, and variations within the scope of the claimed technology and its equivalents.

Other implementations of the clauses described in this section can include a non-transitory computer readable storage medium storing instructions executable by a processor to perform any of the clauses described in this section. Yet another implementation of the clauses described in this section can include a system including memory and one or more processors operable to execute instructions, stored in the memory, to perform any of the clauses described in this section.

The term "turn" references each piece of content communicated by one party (e.g., a doctor) in a conversation with at least one other party (e.g., a patient). For example: Doctor: "Hello. What is the reason for your visit?" (turn 1), Patient: "I have a burning sensation when I urinate." (turn 2), Doctor: "How frequently does this occur?" (turn 3), Patient: "Almost every time I urinate, especially at night." (turn 4), Doctor "That might be a bladder inflammation, a urinary tract infection (UTI), or a prostrate infection." (turn 5), etc.

The systems and techniques described herein provide a set of artificial intelligence (AI) enabled tools for doctors that provide insights and suggestions while the doctor is in conversation with the patient. In this way, the systems and techniques save the doctor time during day-to-day tasks that currently take up much of the doctor's time, e.g., tasks that do not involve seeing patients. While the doctor is in conversation with the patient, the AI may access the patient's electronic medical records (EMR) and repositories of medical knowledge to provide decision support insights, such as suggesting questions for the doctor to ask, suggesting possible diagnoses, suggesting one or more tests to be performed, suggesting a referral to a specialist, performing insurance-related tasks (e.g., looking up appropriate codes) and the like. After the AI determines that the doctor-patient conversation has ended, the AI may document the patient visit, including creating a SOAP note or similar. The note may be created using an off-the-shelf (OTS) template or using a custom template specified by the doctor. The summary of the visit may include a list of potential follow-up actions, such as scheduling a test (e.g., lab work), sending a referral, scheduling a follow-up appointment, and the like. The doctor can review, select, and initiate one or more of the follow-up actions with a few mouse clicks rather than having to manually enter the follow-up actions. For example, the doctor may have a particular specialist (e.g., cardiologist) to whom the doctor refers patients with particular symptoms (e.g., high-blood pressure). In this example, the AI determines, based on the conversation and the patient's medical history, that the patient may have high-blood pressure and predicts based on the doctor's history that the doctor may refer the patient to a cardiologist. The AI may automatically create a referral for the patient to see a particular cardiologist that the doctor prefers and display the referral action in a note summarizing the patient's visit. The referral action displayed in the note enables the doctor to send the referral with a single selection (e.g., via a mouse or other input device), thereby significantly reducing the time spent by the doctor to create and send the referral.

In some cases, the AI may be a generative AI, such as a large language model (LLM) or similar. The AI may include a commercially available AI (e.g., Chat GPT) and may, in some cases, be a hybrid multi-component AI that includes custom AIs and commercially available AIs (e.g., Chat GPT).

The AI may execute on a physical or cloud-based server and send decision support insights via a network to a computing device that is local to the doctor (e.g., a tablet, laptop, or desktop computing device located in the room with the doctor and patient). A multi-modal interface may listen in on the conversation between the doctor and patient and send either audio or a text-based transcription to the AI for analysis. For video and/or audio (telehealth) calls where the doctor and patient are not physically co-located, the interface may listen in to the audio of the conversation (audio or video call) between the doctor and the patient.

The AI may work in the background by ingesting portions (e.g., one or more turns) of the doctor-patient conversation and generating decision support insights based on the patient's medical history (derived from electronic medical records) and established medical knowledge. The decision support insights may include suggestions provided to the doctor in real-time, such as questions the doctor could ask the patient to confirm or rule out particular diagnoses, possible diagnoses (e.g., ranked from most likely to least likely) based on the patient's medical history and current medical knowledge, one or more tests to be performed to confirm or rule out particular diagnoses, a referral to a specialist, and the like. In addition, the doctor may explicitly interact with the AI using a "wake word", such as "Sully" (e.g., similar to "Siri", "Alexa", "Google" or other wake words used to interact with a virtual assistant). For example, the doctor may ask the AI "Sully, does the patient's history indicate that the patient underwent a cardiac ablation?". The AI is able to quickly respond to such questions because the AI has access to the patient's medical records, thereby saving the doctor time from having to perform a manual search of the patient's medical records. For example, the doctor may be seeing the patient for the first time but the patient may have had a previous doctor in another city or state and may have recently moved and so the doctor may be unfamiliar with the patient's complete medical history. As another example, the doctor may use the AI to ascertain information about the patient's history if the patient has difficulty responding to questions because the patient has a medical condition (e.g., autism, suffered a stroke, speech impediment, memory loss, or the like), has a poor grasp of the language in which the doctor communicates, is very young (e.g., a child), or due to another issue. In some cases, the systems and techniques may include a translation module to perform translation to and from a particular language (e.g., Spanish, French, or the like). The AI has access to a large pool of data, including each patient's historical data, such as electronic health records (EHR) and other patient data as well as previous doctor-patient conversations associated with the patient.

The systems and techniques may assist the doctor by generating documentation of a patient visit. After a patient comes in, the patient and the doctor have a conversation which the AI processes. After the AI determines that the patient visit has ended, the AI summarizes the visit by generating a note that is added to the EHR. The AI provides real-time decision support (something that current systems don't do) by listening to the conversation, looking at the patient's history, and generating in real-time suggestions for the doctor, such as what (next) questions the doctor should ask the patient, what might be possible treatment(s), differential diagnosis (to determine a root cause of the issue), possible referrals, possible tests to perform on the patient, and the like. After the visit, the AI creates a note (e.g., SOAP) summarizing the visit and a list of possible actions, such as referrals, lab orders, prescription(s), follow-up appointments, and the like. Without the AI, the doctor would have to review his/her notes, manually create the list of actions, and initiate the actions. By using the systems and techniques, the AI creates the list of actions and the doctor reviews them, selects a subset of the actions, and instructs the AI to perform the selected actions, including any action that a doctor currently performs after a patient visit.

The systems and techniques provide features of a virtual assistant to the doctor. For example, the assistant features may include medical assistant (MA) and research assistant (RA). To illustrate, the doctor sees a patient at a time T1 for which the AI creates a first note. The doctor then sees the patient again for a follow-up at a time T2 for which the AI creates a second note. If the visits are related, the doctor may ask the AI to merge the first note and the second note. The AI is able to determine what to carry forward from the first note, what to discard, and what to replace in first note (e.g., with information from the second note). For example, the patient recently had hip surgery. The first note is a post-surgery exam and says that the hip looks good with no apparent infection. The second note is a follow-up visit in which the doctor notes that while the patient's mobility is good, there is some redness and inflammation in the right hip. Thus, portions ("redness and inflammation") of the second note are used to replace portions ("looks good") of the first note. All conversations and note modifications are logged to provide an audit trail. The systems and techniques are able to provide the various functions described herein very quickly, in real-time, and with a high degree of accuracy.

A challenge when providing decision support insights is how to display the insights to the doctor in a way that doesn't cause the doctor cognitive overload. The systems and techniques described herein use several techniques to display the decision support insights in such a way as to reduce cognitive overload. First, the AI determines an importance (e.g., criticality) of each decision support insight AI and displays insights having an importance greater than a predetermined threshold while suppressing (not displaying) insights having an importance less than or equal to the predetermined threshold. Every insight provided to the doctor has an internally associated importance and this may be used by the user interface (UI) to determine whether to display the insight and if so, how to display the insight. For example, extremely important insights (e.g., suggestions) may be presented using particular properties (e.g., highlight, bold, larger font, different font color, or the like) to highlight the suggestion to the doctor. For example, if the doctor, during the conversation with the patient, says "I will prescribe penicillin" and the patient's history has an indication of an allergic reaction to penicillin then the doctor may be visually alerted "Patient had a reaction to penicillin on <date>". The AI may provide the doctor with suggested questions to ask the patient. For example, the patient has knee pain and the doctor is asking the patient questions. The AI discovers, in the patient's medical history, that the patient had knee surgery on a previous date and suggests that the doctor ask questions related to the surgery. If the AI sends a suggestion for a question while the doctor is asking the same or a similar question, then the AI detects that the question has been asked and sends an update to remove the question and, in some cases, suggests one or more additional follow up questions. If the AI sends a suggestion for a question while the patient volunteers a response to the question, then the AI detects that the question has been answered and sends an update to remove the question and, in some cases, suggests one or more additional follow up questions.

In some cases, the internal importance of an insight may be determined based on a risk (predicted by the AI) and if more than one insight is to be presented to the doctor, the insights may be ranked by the AI according to risk, with the highest risk (most important) insight ranked first and the lowest risk (least important) insight ranked last. Of course, insights with an associated risk below a predetermined threshold may not be displayed. If the doctor misses an important insight when it is first displayed, the AI may adjust the particular properties (e.g., highlight, bold, larger font, different font color, or the like) of the insight to highlight the suggestion to the doctor. In some cases, the insight may be progressively highlighted (e.g., larger font in each subsequent iteration) until the doctor indicates (e.g., verbally or via an input device of a computer) that the doctor has seen the insight.

As previously mentioned, the AI may be a hybrid multi-component AI that includes a one or more custom AIs and one or more commercially available AIs. Historical data, including electronic medical records (EMR) may be provided as input to the AI. In some cases, at least a portion of the patient data may be fed in real-time to the AI. In some cases, doctor-patient conversations associated with a particular doctor may be used to train the AI to enable the AI to chat in a manner similar to the particular doctor. Thus, a doctor's own conversations with patients, CHAT GPT's regular training, and patient EMR records may all be used to train the AI. Complex business logic may be included in a prompt engineering layer of the AI to generate prompts dynamically, verify the output of the AI, and so on. In this way, the AI is able to react in real-time to a doctor-patient conversation.

In some cases, training the AI may include automatic prompt optimization in which a prompt is provided to the AI, the AI generates output, and the same AI model (or a different AI model) rewrites the prompt and looks at the output until a delta between an output and a subsequent output (from the rewritten prompt) is below a threshold.

The systems and techniques include an application programming interface (API) that sits between the AI (LLM) and an endpoint (e.g., a computing device located in the same room as the doctor and patient or tapped into a conversation between the doctor and the patient during a telehealth call). The API takes the doctor-patient conversation as input, sends it to the AI which processes the conversation data and provides outputs, including the decision support insights during the doctor-patient conversation and a note summarizing the conversation after the doctor-patient session has ended.

Triage AI, AI Specialists, Consensus AI, and Response AI

The systems and techniques (also referred to as "architecture") described herein reveal a multiple AI agent consensus architecture to improve diagnostic accuracy and reduce costs in healthcare decision support. Test results show that the systems and techniques outperform individual AI models, such as GPT-40 and Claude 3.7 in accuracy while demonstrating significantly better cost efficiency across multiple standardized medical benchmarks. The systems and techniques use an approach to medical diagnosis that uses AI specialist agent collaboration that mimics the way human medical specialists collaborate. By leveraging smaller, more efficient AI models in the architecture, superior performance is achieved relative to much larger, more expensive AI models. Test results demonstrate superior accuracy of the systems and techniques compared to individual AI models on benchmarks such as the United States Medical Licensing Examination (USMLE) and Medical Multiple-Choice Question Answering (MCQA). The test results indicate greater than 92% accuracy on medical questions and a 60-80% reduction in cost compared to GPT-4 models with equivalent performance. Determining a consensus opinion based on multiple AI specialists results in increased accuracy and enhanced reasoning capabilities. Table 1 compares the accuracy and cost of the consensus model (described herein) with well-known individual commercially available AI models.

TABLE 1

| Model | USMLE Accuracy | MedMCQA Accuracy | Average Confidence | Relative Cost |
|---|---|---|---|---|
| Consensus Model (described herein) | 92% | 90.5% | 97.3% | 1.0x |
| GPT-4o | 86.5% | 85.4% | 95.5% | 3.1x |
| Claude 3.7 | 87.2% | 84.3% | 92.1% | 2.8x |
| MedLM | 84.1% | 82.2% | 91.3% | 2.5x |
| GPT-3.5 Turbo | 79.0% | 78.8% | 89.7% | 0.8x |

The four core architectural components include: (1) a triage AI, (2) multiple AI specialists, (3) a consensus AI, and (4) a response AI. The triage AI monitors the conversation between the doctor and patient, determines relevant AI specialists to listen in to the conversation, and coordinates the consultation process between the AI specialists. The multiple AI specialists include AI models trained in specific medical specialties, such as, for example, cardiology, neurology, nephrology, endocrinology, pediatrics, geriatrics, emergency medicine, ear-nose-throat (ENT), urology, gynecology, orthopedics, cardiology, gastroenterology, pulmonology, hematology, oncology, rheumatology, internal medicine, immunology, and the like that apply different reasoning approaches to a medical problem. The consensus AI evaluates and weighs responses from the AI specialists that are involved with a particular patient. The evaluation and weight is based on confidence (each AI specialist provides a confidence score with their response), reasoning quality (each AI specialist provides reasoning behind their response), and expertise matching (a cardiology AI's opinion may be given greater weight for a patient experiencing heart issues, an orthopedic AI's opinion may be given greater weight if the patient has a fracture, and so on). The response AI produces a final diagnostic output with a confidence score and supporting rationale. It should be understood that the functions of these four components may be further separated or combined. For example, in some cases, one or more of the functions of the triage agent, the consensus AI, and the response AI may be combined.

While listening to the conversation between the doctor and the patient, the triage agent dynamically selects appropriate medical specialists to listen in to the conversation, mirroring real-world medical practice. For example, assume the patient was in an automobile accident and has a concussion, a pneumothorax (a collapsed lung), and a fractured femur. Based on the context (car accident) and the set of symptoms (concussion, pneumothorax, fracture), the triage AI may involve three AI specialists; a neurologist, a pulmonologist, and an orthopedist. Each AI specialist selected by the triage AI is provided access to the doctor-patient conversation as it occurs (typically in N second chunks, N=2–, 30, 60 or the like) and also provided access to a transcript of the doctor-patient conversation from the beginning of the conversation. The access may be to a portion of the audio of the conversation or a transcript of the portion of the audio of the conversation. Each AI specialist, based on their specialty, decides on appropriate treatment protocols, medications, lab work, and the like. The AI specialists may provide questions for the doctor to ask the patient. The consensus AI involves a subset of AI specialists, resulting in a higher score in terms of accuracy of diagnosis. The triage AI determines the context and the set of symptoms and based on those identifies the most relevant specialties from a larger set that includes, for example: Cardiology, Neurology, Emergency Medicine, Infectious Disease, Internal Medicine, Rheumatology, Gastroenterology, Endocrinology, and over 20 additional specialists. This approach results in each medical problem (symptom) receiving attention from the most appropriate expert AI model, substantially increasing diagnostic accuracy. Test results found the accuracy of the individual AI specialists to be between about 87.2% to about 93.5%, with the average accuracy around 90%. The highly accurate performances across specialties demonstrates the system's versatility and comprehensive knowledge base.

The architecture described herein uses a multiple model consensus system. To reduce bias, a diverse set of AI models are used, each with different architectures and training approaches. The diverse set of AI models include: Claude 3.7, GPT-4o mini, DeepSeek R1, Llama 3.3, Qwen-2.5-32B, and other specialized models. In this way, each AI model contributes unique strengths to the diagnostic process. In addition, the use of diverse models results in bias mitigation because the multiple perspectives reduce individual model biases and hallucinations. Each AI model has a temperature setting that defines the predictability of its output. A higher temperature provides more creative results, while a lower temperature produces more predictable responses. In the architecture described herein, fine-tuned temperature settings (typically 0.2) for each AI specialist are used.

Each AI specialist (also referred to as an expert agent) employs three distinct reasoning methodologies to analyze medical questions: (1) clinical reasoning, (2) scientific reasoning, and (3) elimination reasoning. Clinical reasoning uses a patient-centered analysis that focuses on symptoms, clinical presentation, and standard practices. Scientific reasoning uses a mechanism-based analysis based on pathophysiology, biochemistry, and scientific foundations. Elimination reasoning involves a systematic approach to rule out incorrect options through critical analysis. By combining these three approaches, the systems and techniques provide the human doctor with a comprehensive and relevant set of insights.

The systems and techniques use Retrieval-Augmented Generation (RAG). One issue with trained AI models is that their abilities are limited by the training data used to train the AI models and therefore does not include medical knowledge (e.g., papers, test results, newly released pharmaceuticals, and the like) not included in the training data. To overcome this deficiency, the architecture described herein enables the AI specialists to access medical knowledge stored in databases, thereby enabling the AI specialists to access current medical knowledge not included in their training data, referred to as RAG. For example, the AI specialists are provided access to (1) medical guidelines, such as those provided by the Advanced Cardiovascular Life Support (ACLS), the American Heart Association (AHA), Infectious Diseases Society of America (IDSA), and other specialty guidelines, (2) PubMed Research, enabling real-time access to current medical literature, (3) diagnostic criteria such as the latest versions of the Diagnostic and Statistical Manual of Mental Disorders (DSM), International Classification of Diseases (ICD), and the like, (4) pharmacopeia that includes comprehensive medication information, and (5) additional medical knowledge databases. By providing contextually relevant and up-to-date medical knowledge, RAG enhances diagnostic reasoning.

The systems and techniques described herein may include advanced chain of thought (CoT) techniques to improve reasoning transparency in one or more of the AI models. Structured CoT uses systematic and step-by-step diagnostic reasoning. Multi-perspective CoT takes into consideration differential diagnoses from multiple angles. Self-critique CoT involves the AI specialists identifying potential errors in their reasoning. Probabilistic CoT involves each AI specialist providing a quantified confidence level for each diagnostic hypothesis provided by the AI specialist. These enhanced CoT techniques enable better decisions by the various AIs, including the specialists and the consensus AI, and provide transparent reasoning paths.

The systems and techniques described herein may include adversarial testing and red-teaming. The adversarial testing protocol may include: (1) edge case testing in which an AI specialist identifies challenging diagnostic scenarios and (2) bias detection in which an AI specialist tests for demographic and presentation biases. Red-teaming includes actively trying to mislead the system. The systems and techniques may use algorithmically generated difficult test cases to systematically strengthen against potential failure modes and ensure reliable performance in complex clinical scenarios. The systems and techniques system seamlessly integrate into clinical workflows to enable minimal disruption to existing workflows. The AI specialists provide real-time support which is especially critical for difficult. The AI specialists provide specialized insights and generate an AI-based second opinion while the doctor is engaged with the patient in addition to providing alternative diagnostic considerations as well as verifying appropriate treatment selection based on diagnosis.

As a first example, a system includes one or more processors and one or more non-transitory computer-readable storage media to store instructions executable by the one or more processors to perform various operations. The operations include continually receiving, by a triage artificial intelligence, a portion of a conversation between a doctor and a patient. The triage artificial intelligence comprises a large language model that has been trained using training data that includes multiple audio conversations between doctors and patients. The operations include determining, by the triage artificial intelligence, that the conversation includes a first set of trigger words associated with a first symptom of the patient. The operations include selecting, by the triage artificial intelligence and based on the first set of trigger words associated with the first symptom, a first artificial intelligence specialist in a first medical specialty from a plurality of artificial intelligence specialists. The operations include providing the first artificial intelligence specialist with access to the conversation between the doctor and the patient. The operations include determining, by the triage artificial intelligence, that the conversation includes a second set of trigger words associated with a second symptom of the patient. The operations include selecting, by the triage artificial intelligence and based on the second set of trigger words associated with the second symptom, a second artificial intelligence specialist in a second medical specialty from the plurality of artificial intelligence specialists. The operations include providing the second artificial intelligence specialist with access to the conversation between the doctor and the patient. The operations include determining, by the consensus artificial intelligence, a consensus answer to a set of questions sent to a subset of the plurality of artificial intelligence specialists that includes the first artificial intelligence specialist and the second artificial intelligence specialist. The operations include providing the consensus answer to a continually updated graphical user interface of a computing device associated with the doctor. The consensus answer is displayed using a text-based presentation that has a different graphical presentation than other information displayed by the graphical use interface. The operations include retraining the triage artificial intelligence using at least the conversation between the doctor and the patient. Determining the consensus answer to the set of questions sent to the subset of the plurality of artificial intelligence specialists may include: (1) sending, by the consensus artificial intelligence, the set of questions to the subset of the plurality of artificial intelligence specialists, where the subset of the plurality of artificial intelligence specialists were each provided with access to the conversation between the doctor and the patient and (2) receiving a set of answers, by the consensus artificial intelligence and from the subset of the plurality of artificial intelligence specialists with access to the conversation between the doctor and the patient, where individual answers from the set of answers correspond to individual questions in the set of questions. The operations may include receiving, by the consensus artificial intelligence and from the subset of the plurality of artificial intelligence specialists with access to the conversation between the doctor and the patient, a confidence level associated with individual answers from the set of answers. The operations may include determining, by the consensus artificial intelligence, the consensus answer to individual questions in the set of questions based at least in part on using the confidence level to weight individual answers from the set of answers. The operations may include assigning, by the consensus artificial intelligence and based on the symptom associated with the individual answers, a specialist weight to the individual specialists in the subset of the plurality of artificial intelligence specialists with access to the conversation between the doctor and the patient. The operations may include determining, by the consensus artificial intelligence, a consensus answer to individual questions in the set of questions based at least in part on using the confidence level as a first weight and the specialist weight as a second weight to individual answers from the set of answers. The operations may include accessing, by the first artificial intelligence specialist, current medical knowledge in one or more medical knowledge databases and performing, by the first artificial intelligence specialist, retrieval augmented generation (RAG) to create one or more decision support insights. Individual artificial intelligence specialists in the plurality of artificial intelligence specialists are configured to use one or more chain of thought techniques. For example, the one or more chain of thought techniques may include: structured chain of thought that uses step-by-step diagnostic reasoning, multi-perspective chain of thought that takes into consideration differential diagnoses from multiple angles, self-critique chain of thought that involves identifying potential errors in the individual artificial intelligence specialists own reasoning, probabilistic chain of thought that involves individual artificial intelligence specialists providing a confidence level for each diagnostic hypothesis provided, or any combination thereof. The operations may include disabling access to the conversation between the doctor and the patient for the first artificial intelligence specialist based on determining, by the triage artificial intelligence, that the conversation is no longer discussing the first symptom.

As a second example, a computer-implemented method includes continually receiving, by a triage artificial intelligence, a portion of a conversation between a doctor and a patient. The triage artificial intelligence comprises a large language model that has been trained using training data that includes multiple audio conversations between doctors and patients. The computer-implemented method includes determining, by the triage artificial intelligence, that the conversation includes a first set of trigger words associated with a first symptom of the patient. The computer-implemented method includes selecting, by the triage artificial intelligence and based on the first set of trigger words associated with the first symptom, a first artificial intelligence specialist in a first medical specialty from a plurality of artificial intelligence specialists and providing the first artificial intelligence specialist with access to the conversation between the doctor and the patient. The computer-implemented method includes determining, by the triage artificial intelligence, that the conversation includes a second set of trigger words associated with a second symptom of the patient. The computer-implemented method includes selecting, by the triage artificial intelligence and based on the second set of trigger words associated with the second symptom, a second artificial intelligence specialist in a second medical specialty from the plurality of artificial intelligence specialists and providing the second artificial intelligence specialist with access to the conversation between the doctor and the patient. The computer-implemented method includes determining, by the consensus artificial intelligence, a consensus answer to a set of questions sent to a subset of the plurality of artificial intelligence specialists that includes the first artificial intelligence specialist and the second artificial intelligence specialist and providing the consensus answer to a continually updated graphical user interface of a computing device associated with the doctor. The consensus answer is displayed using a text-based presentation that has a different graphical presentation than other information displayed by the graphical use interface. The computer-implemented method includes retraining the triage artificial intelligence using at least the conversation between the doctor and the patient. Determining, by the consensus artificial intelligence, the consensus answer to the set of questions sent to the subset of the plurality of artificial intelligence specialists may include (1) sending, by the consensus artificial intelligence, the set of questions to the subset of the plurality of artificial intelligence specialists, where the subset of the plurality of artificial intelligence specialists were each provided with access to the conversation between the doctor and the patient and (2) receiving a set of answers, by the consensus artificial intelligence and from the subset of the plurality of artificial intelligence specialists with access to the conversation between the doctor and the patient. Individual answers from the set of answers correspond to individual questions in the set of questions. The computer-implemented method may include receiving, by the consensus artificial intelligence and from the subset of the plurality of artificial intelligence specialists with access to the conversation between the doctor and the patient, a confidence level associated with individual answers from the set of answers and determining, by the consensus artificial intelligence, the consensus answer to individual questions in the set of questions based at least in part on using the confidence level to weight individual answers from the set of answers. The computer-implemented method may include assigning, by the consensus artificial intelligence and based on the symptom associated with the individual answers, a specialist weight to the individual specialists in the subset of the plurality of artificial intelligence specialists with access to the conversation between the doctor and the patient and determining, by the consensus artificial intelligence, the consensus answer to individual questions in the set of questions based at least in part on using the confidence level as a first weight and the specialist weight as a second weight to individual answers from the set of answers. The computer-implemented method may include based on determining, by the triage artificial intelligence, that the conversation is no longer discussing the second symptom, disabling access to the conversation between the doctor and the patient for the second artificial intelligence specialist. Medical specialties associated with the plurality of artificial intelligence specialists may, for example, include: cardiology, neurology, nephrology, endocrinology, pediatrics, geriatrics, emergency medicine, ear-nose-throat (ENT), urology, gynecology, orthopedics, gastroenterology, pulmonology, hematology, oncology, rheumatology, internal medicine, and immunology. Individual artificial intelligence specialists in the plurality of artificial intelligence specialists may be configured to use: (1) clinical reasoning by performing a patient-centered analysis based on symptoms, clinical presentation, and standard medical practices, (2) scientific reasoning by performing a mechanism-based analysis based on pathophysiology, biochemistry, and scientific foundations, and (3) elimination reasoning using an adversarial testing protocol in which edge cases are tested and bias detection is performed for demographic bias and presentation bias.

As a third example, one or more non-transitory computer-readable storage media store instructions executable by one or more processors to perform various operations. The operations include continually receiving, by a triage artificial intelligence, a portion of a conversation between a doctor and a patient. The triage artificial intelligence comprises a large language model that has been trained using training data that includes multiple audio conversations between doctors and patients. The operations include determining, by the triage artificial intelligence, that the conversation includes a first set of trigger words associated with a first symptom of the patient. The operations include selecting, by the triage artificial intelligence and based on the first set of trigger words associated with the first symptom, a first artificial intelligence specialist in a first medical specialty from a plurality of artificial intelligence specialists. The operations include providing the first artificial intelligence specialist with access to the conversation between the doctor and the patient. The operations include determining, by the triage artificial intelligence, that the conversation includes a second set of trigger words associated with a second symptom of the patient. The operations include selecting, by the triage artificial intelligence and based on the second set of trigger words associated with the second symptom, a second artificial intelligence specialist in a second medical specialty from the plurality of artificial intelligence specialists and providing the second artificial intelligence specialist with access to the conversation between the doctor and the patient. The operations include determining, by the consensus artificial intelligence, a consensus answer to a set of questions sent to a subset of the plurality of artificial intelligence specialists that includes the first artificial intelligence specialist and the second artificial intelligence specialist. The operations include providing the consensus answer to a continually updated graphical user interface of a computing device associated with the doctor. The consensus answer is displayed using a text-based presentation that has a different graphical presentation than other information displayed by the graphical use interface. The operations include retraining the triage artificial intelligence using at least the conversation between the doctor and the patient. Determining, by the consensus artificial intelligence, the consensus answer to the set of questions sent to the subset of the plurality of artificial intelligence specialists may include: (1) sending, by the consensus artificial intelligence, the set of questions to the subset of the plurality of artificial intelligence specialists, where the subset of the plurality of artificial intelligence specialists were each provided with access to the conversation between the doctor and the patient and (2) receiving a set of answers, by the consensus artificial intelligence and from the subset of the plurality of artificial intelligence specialists with access to the conversation between the doctor and the patient. Individual answers from the set of answers correspond to individual questions in the set of questions. The operations may include receiving, by the consensus artificial intelligence and from the subset of the plurality of artificial intelligence specialists with access to the conversation between the doctor and the patient, a confidence level associated with individual answers from the set of answers and determining, by the consensus artificial intelligence, the consensus answer to individual questions in the set of questions based at least in part on using the confidence level to weight individual answers from the set of answers. The operations may include assigning, by the consensus artificial intelligence and based on the symptom associated with the individual answers, a specialist weight to the individual specialists in the subset of the plurality of artificial intelligence specialists with access to the conversation between the doctor and the patient. The operations may include determining, by the consensus artificial intelligence, the consensus answer to individual questions in the set of questions based at least in part on using the confidence level as a first weight and the specialist weight as a second weight to individual answers from the set of answers. The individual artificial intelligence specialists in the plurality of artificial intelligence specialists may be configured to use one or more of: (1) clinical reasoning by performing a patient-centered analysis based on symptoms, clinical presentation, and standard medical practices, (2) scientific reasoning by performing a mechanism-based analysis based on pathophysiology, biochemistry, and scientific foundations, and (3) elimination reasoning using an adversarial testing protocol in which edge cases are tested and bias detection is performed for demographic bias and presentation bias. The operations may include accessing, by the first artificial intelligence specialist, current medical knowledge in one or more medical knowledge databases and performing, by the first artificial intelligence specialist, retrieval augmented generation (RAG) to create one or more decision support insights.

FIG. 1 is a block diagram of a system 100 illustrating an artificial intelligence (AI) receiving a portion of a conversation between a doctor and a patient and generating decision support insights for the doctor, according to some implementations. The system 100 includes a computing device 102 connected to a server 104 via one or more networks 106. The server 104 may access one or more electronic medical records (EMR) 108 via the network 106. The server 104 may access one or more medical knowledge databases 110 via the network 106. The server 104 includes an triage agent 111 and one or more artificial intelligence (AI) 112. In some cases, the AI 112 may be implemented using a generative AI, such as a large language model (LLM) or similar.

The system 100 illustrates the interaction between the computing device 102 and the server 104 at two different times, at a time 122(1) and at a time 122(N) (N>1) that occurs after the time 122(1) (N>0, N=minutes). The events that occur at the time 122(N) are referred to as downstream relative to events that occur at the time 122(1). The events that occur at the time 122(1) are referred to as upstream relative to events that occur at the time 122(N). The server 104 multiple artificial intelligence (AI) agents, such as, for example, a triage AI 111, a consensus AI 148, a response AI 150, and multiple AI specialists 112. One or more of the AI models 111, 112, 148, 150 may be implemented using multiple AI models (e.g., commercial and custom AI models), such as large language models (LLMs).

The computing device 102 may be a tablet computing device, a laptop, a desktop, a smart phone, or another type of computing device that a doctor 118 uses when seeing patients, such as a representative patient 120. If the patient 120 has provided a reason as to why the patient 120 has made an appointment with the doctor 118, the triage AI 111 may determine the reason by accessing the electronic medical records 108. The triage AI 111 may access the electronic medical records 108 associated with the patient 120 to determine the patient's medical history.

The AI specialists 112 may use retrieval-augmented generation (RAG) to access the medical knowledge database 110 regarding information relevant to the patient's reason for visiting the doctor and relevant to the patient's medical history before generating an opinion. Based on the reason for the patient's visit, the patient's history, and the medical knowledge in the medical knowledge databases 110, the AI 111, 112, 148, 150 may provide output 126(1) to the computing device 102 that is displayed as at least one decision-support insight 112(1). For example, if the patient's reason for the current visit to the doctor 118 is lower back pain and the patient's history, accessed via the EMR 108, indicates a history of back pain, then the decision support insights 140(1) may include questions ("Are you stretching your hamstrings regularly?") to ask the patient 120 and a possible prescription (e.g., for a muscle relaxant that the patient has responded to in the past). In this way, the doctor 118 may review the decision support insights 140(1) while in conversation with the patient 120.

An interface 114 associated with the computing device 102 may capture a portion 116(1) (e.g., X seconds, such as 10, 20, 30, or the like) of a conversation between the doctor 118 and the patient 120. For example, the portion 116(1) of the conversation may include one or more turns between the doctor 118 and the patient 120. The computing device 102 may receive the portion 116(1) from the interface 114 and send the data 124(1) to the server 104 for processing by the AI 112. The data 124(1) may be (1) audio data of the portion 116(1) of the conversation captured by a microphone of the interface 114, (2) a text-based transcript 152 of the portion 116(1) created by a speech-to-text module executed by the computing device 102, or (3) any combination thereof. Of course, in some cases, the speech-to-text module may be executed by the server 104. In such cases, the computing device 102 may send audio data (in the data 124(1)) to the server 104 and the server 104 may convert the audio data to text for the AI 112 before using the text of the conversation as input. Thus, the AI 111, 112, 148, 150 may be trained using text-based data, audio-based data, or a combination of both.

The interface 114 may capture biometrics 142 associated with the patient 120 such as, for example, blood pressure (from a blood pressure monitor), pulse (from a pulse rate monitor), electrocardiogram (ECG) data (from an ECG machine), body temperature (from a thermometer), oxygen level (from an oximeter), and other biometric data. The interface 114 may include the biometrics 142 in the data 124 sent to the server 104.

The AI 112 receives the data 124(1) including the biometrics 142(1) and the portion 116(1) of the conversation between the doctor 118 and the patient 120 and produces raw output 126(N) (N>0), including decision support insights 140(N), based on the data 124(1), the patient's history (as derived from the EMR 108), and the medical knowledge databases 110. For example, based on the data 124(1), the AI 111, 112, 148, 150 may provide suggestions 138 that include one or more additional questions for the doctor 118 to ask the patient 120, suggest one or more tests (e.g., EKG or echocardiogram for heart-related issues) that the doctor 118 should consider performing on the patient 120, suggest one or more referrals (e.g., referral to a specialist, such as a cardiologist for heart-related issues, a gastroenterologist for digestive-related issues, an ophthalmologist for eye-related issues, and so on), suggested diagnoses (e.g., high blood pressure), suggested prescriptions (e.g., diuretic, calcium channel blocker, ace inhibitor, or angiotensin receptor blocker for high blood pressure), and the like. In some cases, the AI 112 may update the doctor on possible contraindications. For example, assume the patient 120 is describing symptoms related to high blood pressure and the doctor 118 is proposing to put the patient 120 on a diuretic. The AI specialists 112 may include an AI cardiologist that the triage AI 111 has enabled to access the data 124. The AI cardiologist 112 may determine, based on the patient's history, that the patient 120 has previously suffered from gout. The AI cardiologist 112 may further determine, based on the medical knowledge databases 110, that a diuretic may cause a recurrence of gout. In such cases, the AI cardiologist 112 may include, in the suggestions 138, an indication that the patient 120 has previously suffered from gout, an indication that the diuretic may cause the gout to recur and suggest an alternative blood pressure medication that is less likely to aggravate the gout or may suggest prescribing allopurinol to reduce the possibility of gout reoccurring.

The computing device 102 may perform post processing 128 of the output 126(N) to derive and present one or more of decision support insights 140(N), adjustments 132, prioritization 134, presentation 136, and suggestions 138. In some cases, the computing device 102 may provide a translation 130 from one language (e.g., used by the doctor 118) to another language (e.g., used by the patient 120). For example, the translation 130 may perform (1) Spanish to English translation and (2) English to Spanish translation when the doctor 118 speaks English and the patient 120 speaks Spanish. While the post processing 128 and the translation module 130 are illustrated as being executed by the computing device 102, in some cases one or both of the post processing 128 and the translation 130 may be executed by the server 104.

The suggestions 138 may include questions for the doctor 118 to ask the patient 120, suggestions for one or more tests for the patient 120, suggestions for one or more referrals, suggested diagnoses, suggested prescriptions, and other insights derived from the portion 116(1), the EMR 108, and the medical knowledge databases 110. In some cases, the output 126(N) may specify one or more adjustments 132 to previously provided decision support insights, such as the decision support insights 140(1). For example, the portion 116(1) of the conversation may cause the AI 111, 112, 148, 150 to provide a particular suggestion. At approximately the same time, the particular suggestion may occur to the doctor 118. The doctor 118 may utter the particular suggestion (e.g., a particular diagnoses, a particular question, or the like) in a subsequent portion 116 (e.g., the portion 116(N)) of the conversation. After receiving the subsequent portion 116 of the conversation that includes the particular suggestion, the AI 111, 112, 148, 150 may determine that the doctor 118 has provided the particular suggestion and include in the adjustments 132 an instruction to delete the particular suggestion from the suggestions 138 or the decision support insights 140(N) displayed to the doctor 118. As another example, the portion 116(1) of the conversation may cause the AI 111, 112, 148, 150 to provide a particular suggestion. At approximately the same time, the patient 120 may volunteer information related to particular suggestion in a subsequent portion 116 of the conversation. For example, assume the particular suggestion includes a question for the doctor 118 to ask the patient 120 and the patient, during the subsequent portion 116 of the conversation, volunteers (e.g., without the doctor 118 asking) the answer to the question. After receiving the subsequent portion 116 of the conversation that includes the answer to the question, the AI 111, 112, 148, 150 may determine that the doctor 118 should not ask the question and include in the adjustments 132 an instruction to delete the particular suggestion (to ask the question) from the suggestions 138 or the decision support insights 140(N) displayed to the doctor 118. In these examples, the AI 111, 112, 148, 150 may determine that a suggestion to ask the patient a particular question can be removed because either the doctor 118 asked the question or the patient 120 volunteered information answering the question. To illustrate, if the doctor 118 determines that the patient 120 is likely suffering from high blood pressure and is considering prescribing a diuretic, the AI AI 111, 112, 148, 150 may provide in the suggestions 138 that the doctor 118 ask the patient 120 if the patient has previously suffered from gout. Before or while the suggestions 138 are being displayed by the computing device 102, the doctor 118 may ask the patient 120 whether the patient 120 has previously suffered from gout. Alternately, before or while the suggestions 138 are being displayed by the computing device 102, the patient 120 may volunteer that the patient 120 has previously suffered from gout. In either case, the AI 111, 112, 148, 150 determines that the suggestion to the doctor 118 to ask the patient 120 the question (whether the patient 120 has previously suffered from gout) is no longer applicable and includes an instruction in the adjustments 132 to remove that particular question from the suggestions 138 or the decision support insights 140(N).

The prioritization 134 may prioritize the suggestions 138, the decision support insights 140(N) or both based on a criticality score assigned to each of the decision support insights 140(N) based on medical urgency. The prioritization 134 may occur in different ways based on presentation logic 136. The presentation logic 136 may include preferences of the doctor 118 on how the decision support insights 140(N) are presented. For example, the presentation logic 136 may reorder the suggestions 138 based on the criticality score such that suggestions with a higher score are placed higher while suggestions with the lower score are placed lower in the list of suggestions 138. As another example, the presentation logic 136 may color code the suggestions 138 based on the criticality score. In this example, suggestions with a higher score may be displayed with a particular color or font size compared with suggestions having a lower score. To illustrate, a critical suggestion may be displayed in a larger font or in bold font while less critical suggestions may be displayed in a smaller font or in a normal (non-bold) font. In this way, the presentation logic 136 may use the prioritization 134 to determine how and in what order the decision support insights 140(N) are displayed to the doctor 118, thereby enabling the doctor 118 to visually identify critical decision support insights.

Of course, the process may continue with another portion 116(N) of the conversation between the doctor 118 and the patient 120 being captured by the interface 114 and sent to the AI 111, 112, 148, 150 as the data 124(N) for additional processing. Thus, the AI 111, 112, 148, 150 may continually receive portions of the conversation between the doctor 118 and the patient 120 and continually provide the output 126 for display to the doctor 118 as the decision support insights 140. This process continues until the AI 111, 112, 148, 150 determines that the conversation has ended, typically after determining that one or both of the doctor 118 or the patient 120 has left the room or is no longer participating in a telehealth call. As previously mentioned, the conversation between the doctor 118 and the patient 120 may occur physically in a room, such as an examination room associated with the doctor 118 or virtually via a telehealth call, such as a video call or an audio call. The AI 111, 112, 148, 150 provides the output 126 to a display device associated with the computing device 102 that the doctor 118 can view but that the patient 120 may not view.

Triage AI, Consensus AI, and AI Specialists

The interface 114 receives the audio portion 116 of a conversation between the doctor 118 and the patient 120 in real-time. The audio portion 116 may be transcribed by the interface 114, the computing device 102, or the server 104. In this way, one or more of the AI 111, 112, 148, 150 receive a transcribed portion of the audio portion 116.

During the conversation, the triage AI 111 examines the content of the portion 116 of the conversation and selects a subset 146 of one or more AI specialists 112 to listen to the conversation and provide insights to the doctor 118. The triage AI 111 may determine a context 164 and a set of (one or more) symptoms 166 associated with the patient. Typically, the triage 111 may select one to three AI specialists 112 for the subset 146. Each AI specialist 112 is trained using a particular body of knowledge in their specialty. During the conversation, the triage AI 111 may switch the AI specialists 112 in and out of the subset 146, depending on what is being discussed. Some AI specialists 112 may be present during the entire conversation while others may be brought in and out of the subset 146 that has access to the conversation. For example, if a particular AI specialist 112 is no longer relevant to the context 164, then the particular specialist may be taken out and another specialist brought in. To illustrate, when topic #1 is being discussed, the triage AI 111 detects a set of (one or more) words associated with topic #1 in the portion 116 of the conversation, causing the triage AI 111 to bring in AI specialist #1. After determining that the conversation has moved from topic #1 to topic #2, the triage AI 111 may remove AI specialist #1 and bring in AI specialist #2. Typically, a patient may have up to 3 complaints. For example, assume the patient 120 has been in an automobile accident, in which the patient 120 has a concussion, a pneumothorax (a collapsed lung), and a fractured femur. Based on detecting the word "concussion" spoken by the doctor 118 in the conversation, the triage AI 111 brings in an AI neurologist (from the AI specialists 112) into the subset 146. Based on detecting the trigger word "pneumothorax" (or the set of trigger words "collapsed lung") spoken by the doctor 118 in the conversation, the triage AI 111 brings in an AI pulmonologist (from the AI specialists 112) into the subset 146. Based on detecting the trigger word "fracture" (or the set of trigger words "fractured <bone name>") spoken by the doctor 118 in the conversation, the triage AI 111 brings in an AI orthopedist (from the AI specialists 112) into the subset 146. The AI specialists in the subset 146 access the current portion 116 of the conversation and the transcript 152 of the conversation from the beginning of the conversation until the present time. Each AI specialist in the subset 146 independently determines treatment protocols, medications, lab work, and other details related to their specialty and provides a portion of the output 126 that includes a diagnosis based on their specialty. The consensus AI 148 reviews the diagnosis, including reasoning, from each AI specialist in the subset 146 and determines a final diagnosis, resulting in a higher score in terms of accuracy of diagnosis. This final diagnosis is presented to the doctor 118 as one of the decision support insights 140. The triage AI 111 uses specific logic to choose the specialists in the subset 146. The flow of data 124, derived from the conversation between the doctor 118 and the patient 120, is routed to the AI specialists in the subset 146. The triage AI 111 selects the specialist(s) based on determining that the conversation includes certain trigger word(s). For example, if the conversation includes "broken" and "bone" in close proximity, then triage AI 111 brings in an orthopedic specialist. The context 164 (e.g., car accident) and the set of symptoms 166 (concussion, broken femur, difficulty breathing) drive the selection of the AI specialists for the subset 146.

When the triage AI 111 determines that a first AI specialist is no longer relevant to conversation, e.g., because the conversation has moved from a first topic associated with the first AI specialist, the triage AI 111 may remove the AI specialist from the subset 146. If the conversation has moved to a second topic, the triage AI 111 may bring in another (different) AI specialist. Changing which AI specialist are included or removed from the subset 146 happens in real time. The triage AI 111 move AI specialists in and out of the subset 146 based on the conversation (the data 124).

In the example of the patient who was in a car accident, the AI accessing the conversation between the doctor 118 and the patient 120 include the triage AI 111 which brings in (to listen in on the conversation) the subset 146 that includes an AI pulmonologist, an AI neurologist, and an AI orthopedic specialist. Each of the individual AIs may come up with follow up questions, differentials, protocols, tests, medications, referrals and the like which are presented as decision support insights 140 to the doctor 118. The triage AI 111 coordinates the subset 146 of AI specialists while the doctor 118 is engaged in conversation with the patient 120. The consensus AI 148 coordinates the recovery plans (provided by the subset 146 of AI specialists) for the pulmonary, neurological, and orthopedic injuries. While the triage AI 111, the consensus AI 148, and the response AI 150 are shown as separate, in some cases, one or more of their functions may be combined or the functions may be divided differently than described herein.

After the triage AI 111 determines that the conversation between the doctor 118 and the patient 120 has ended, the consensus AI 148 receives opinions from each AI specialist that was brought in to the subset 146 during the conversation and weights the opinions (if more than one AI specialist was brought in to the subset 146). The primary function of the triage AI 111 is to determine which of the AI specialists 112 are relevant to the current portion of the conversation and which are no longer relevant. The consensus AI 148 and the response AI 150 use a fine-tuned model that is trained on the interactions between actual patients and doctors and how the doctor proceeds at the conclusion of each interaction. The doctors in the training data decide the diagnosis, medications, labs, and other actions and this is included in each doctor's clinical notes. What each doctor in the real world does may vary from what is in textbooks because of the doctor's experience. Training using real world doctor-patient interactions differentiates the consensus AI 148 and the response AI 150 from AI models that are just trained using medical textbooks. In the system 100, The model is trained using textbooks as well as doctors actual encounters with patients. For example, the consensus AI 148 and the response AI 150 are trained using both medical textbooks and real world encounters. Thus, the consensus AI 148 and the response AI 150 are trained regarding off-label use for medications and other real world information.

Each of the AI specialists 112 has been trained on the transcripts from conversations between doctors (in each specialty) and patients and then fine-tuned using the doctor's final notes that include the final diagnosis, the final protocols that were performed, the lab procedures that were performed, and other decisions made by the doctor. By training the AI specialists 112 using real world training data (rather than just textbook-based medical knowledge), the AI specialists 112 are trained in how medicine is actually practiced in the field, such as off-label uses of medications and the like. Thus, the AI specialists 112 take into account both textbook knowledge and real-world practicality to provide primary insights and secondary insights to the doctor 118. In some cases, the AI specialists 112 may use retrieval-augmented generation (RAG) 154, a technique that improves the accuracy of Large Language Models (LLMs) by connecting them with external knowledge bases (the medical knowledge databases 110), enabling each AI to provide more accurate, relevant, and up-to-date responses by first retrieving information from those sources before generating output. The AI specialists 112, after receiving the data 124 (part of the conversation), may perform a search to retrieve relevant information from the medical knowledge databases 110. The retrieved information is used by the AI specialists 112 when generating a response (output 126). RAG 154 enables the AI specialists 112 to access and incorporate external knowledge, such as knowledge that was not included in their training data), thereby improving the accuracy and relevance of their respective outputs. RAG 154 addresses the limitations of LLMs. The LLMs are trained on large datasets but may be missing medical knowledge discovered after the LLMs were trained. By incorporating external knowledge from the medical knowledge databases 110, RAG 154 helps the AI specialists 112 provide more accurate and contextually relevant responses. RAG 154 may reduce the tendency of LLM, such as the AI specialists 112, to "hallucinate" and produce incorrect information by grounding the output of the AI specialists 112 in verified medical data. RAG 154 enables the AI specialists 112 to incorporate the latest medical knowledge without having to retrain the AI specialists 112. In this way, the time between retraining AI specialists 112 can be increased without significant negative consequences. Each AI specialist 112 is trained on a body of knowledge and uses RAG 154 to augment inference by accessing external knowledge that the AI specialist may not have been trained on. In some cases, the AI specialists in the subset 146 may interact with each other, e.g., a first AI specialist gives their opinion to a second AI specialist or asks the second AI specialist a question.

How much creativity each AI specialist 112 has may vary depending on the AI specialist. The AI specialists 112 are logical and follow all protocols but the creativity of individual AI specialists may vary. Each of the AI specialists 112 may use several different types of reasoning, including clinical reasoning, scientific reasoning, and elimination reasoning. Clinical reasoning is what an actual physician would do in an examination room. The physician thinks through the problem. What the physician does is based off of the presentation, what the set of symptoms 166 are, what the patient is saying, what the lab results are, and so on, to come to a conclusion. Scientific reasoning is based off of literature, but also more off of the first few years of medical school, e.g., microbiology, pathology, histology, biochemistry, biochemical pathways for reactions, and so on. These are things that a physician learned in medical school but doesn't think about when they're in practice. The AI specialists 112 use scientific reasoning because considering this type of information can be useful, particularly for edge cases. In some cases, the scientific reasoning may enhance the clinical reasoning. In elimination reasoning, each AI specialist thinks things through and eliminates what is highly unlikely based on each AI specialist's conclusions and, in some cases, based off of reviewing the conclusions of the subset 146 of AI specialists that were brought in. All of this occurs before the response AI 150 makes a final decision. The response AI 150 takes into account the opinions (and associated reasoning) of the AI specialists and provides an output that determines the decision support insights 140 provided as a conclusion. Elimination reasoning may use adversarial testing and red-teaming to eliminate unlikely conclusions. Elimination reason may include adversarial reasoning and self-critique. Adversarial reasoning involves one AI specialist's output being critically evaluated by other AI specialists (included in the subset 146) to balance out biases and prevent overreliance on a single AI specialist's output. Self-critique means individual AI specialists actively identify weaknesses in their own reasoning.

Each AI specialist, when added to the subset 146, has access to the full text (transcript 152) of the conversation up to that point (from the beginning). Each AI specialist also receives a transcription (data 124) of the portion 116 of the conversation, typically chunked out approximately every 20 seconds. To reduce time for AI specialists to come up to speed (and reduce latency), in some cases, the triage AI 111 may, based on an initial assessment of the patient 120, which AI specialists are likely to be involved and provide them with access to the conversation before bringing the AI specialists into the subset 146. In some cases, the AI specialists may work in isolation while in other cases the AI specialists may communicate with each other by asking questions, offering an opinion, or the like. At the end of the conversation between the doctor 118 and the patient 120, each AI specialist that was included in the subset 146 provides an opinion. After the AI specialists included in the subset 146 have each come up with an opinion, the AI specialists may discuss their respective conclusions amongst themselves and, in some cases, may alter their conclusions based on the discussion.

The consensus AI 148 assimilates the output provided by the AI specialists in the subset 146. Each AI specialist in the subset 146 is well versed in their particular area of medicine. In contrast, the consensus AI 148 assimilates the output from the AI specialists in the subset 146 and makes a final decision on the final diagnosis and makes a plan moving forward, including prioritizing the various outputs from the AI specialists. In the car accident example, the most important thing is pulmonology, because the collapsed lung, if not treated in a timely manner, will decompensate the patient. In this example, the outputs of the neurologist AI and the orthopedic AI are secondary to the output of the pulmonologist AI. In this way, the system 100 is able to provide decision support insights that reflect the output of multiple AI specialists, something that is not possible when using a single AI. Thus, the combination of the triage AI 111, the AI specialists 112, and the consensus AI 148 are able to provide the doctor 118 with a comprehensive plan that takes into account all of the patient's set of symptoms 166 (e.g., pneumothorax, broken femur, concussion) and prioritizes each symptom's treatment.

In some cases, the triage AI 111 and/or the consensus AI 148 may generate questions 156 for the AI specialists in the subset 146 and analyze answers 158 from the AI specialists. The questions 156 may include multiple choice questions, binary response questions (response is either yes or no), one phrase response questions (what, in your opinion, is the most important diagnosis), or other types of questions. For example, the answers 158 may be used by the triage AI 111 to determine an order (from most serious to least serios) in which to analyze the set of symptoms 166 of the patient 120. In this way, potentially life threatening symptoms (e.g., collapsed lung) may be dealt with before other symptoms.

The consensus AI 148 is trained on how clinicians actually practice medicine, meaning that it's trained on the transcripts of conversations that physicians have with patients and what the physician has decided to do based off of their conversation with the patient. The consensus AI 148 receives the outputs of all of the AI specialists in the subset 146. The consensus AI 148 determines the major insights to provide the doctor 118 during their interaction with the patient 120, what questions the patient 120 should be asked and in what order, what protocols need to be assessed immediately, and so on.

After determining that the conversation has ended, the consensus AI 148 looks at the entire conversation, along with the opinions (including reasoning behind the opinions) and prioritizes the needs of the patient 120 accordingly. The consensus AI 148 weights each specialist AI's opinion based on the conversation. For example, if a person in a car accident has a broken rib and is having breathing issues, then that is the main focus initially (because it could cause the most damage if left untreated) and everything else is secondary. Thus, the consensus AI 148 makes a conclusion at the end of the conversation in real time. The AI specialists make assessments and provide reasoning for their assessments, which the consensus AI 148 uses to provide a final plan. The consensus AI 148 makes the final decision, similar to an attending physician, at the end of the conversation. In straightforward cases, one AI specialist may be brought in to the subset 146 but for more complicated cases, multiple AI specialists may be brought in. Typically, in complicated cases, there may be 3 to 5 AI specialists, at any given point in time during the conversation, in the subset 146. The multiple opinions from multiple AI specialists results in improved outcomes for patients.

After determining that the conversation has ended, each of the AI specialists 112 that were brought in to the subset 146 to listen to the conversation may be asked multiple choice questions 156 by the consensus AI 148. Each AI specialist 112 independently provides an answer 158 to the multiple-choice questions 156, and the consensus AI 148 selects an answer that is chosen by the majority as a consensus answer 162 that is provided to the doctor 118. In some cases, to further improve accuracy, each AI specialist 112 may provide a confidence level 160 for each answer 158 and the consensus AI 148 may use the confidence level 160 to weight each of the answers 158. Each AI specialist 112 provides the answer 158 to each multiple choice question 156 and provides an associated confidence level 160 for each answer. The answer 158 (to each multiple choice question 156) provided by one of the AI specialists 112 is weighted based on the confidence level 160 associated with the answer 158. Thus, when an AI specialist 112 expresses a higher confidence level 160 in a particular answer 158, the particular answer 158 is given more influence. The consensus AI 148 determines the consensus answer 162 based on a weighted score of the answers 158 and associated confidence level 160 as the final answer. Providing the confidence level 160 enables the AI specialists 112 with strong predictions to influence the final answer. In some cases, the consensus agent 148 will first assess the multiple choice question 156 and assign an additional weight to each AI specialist 112 (that was brought into the subset 146) to further boost the confidence weighting. For example, for a question related to a particular specialty, the response of an AI specialist associated with the particular specialist may be given great weight than the answers of other AI specialists. To illustrate, for a question related to bones, the answer provided by the orthopedic AI specialist may be given greater weight than other AI specialists, for a question related to lungs/breathing, the answer provided by the pulmonologist AI specialist may be given greater weight than other AI specialists, for a question that is cardiovascular-related, the answer provided by the cardiologist AI specialist may be given greater weight than other AI specialists, and so on. The weighted score may be determined as follows (assuming M number of AI specialists, M>0):

$$\text{Weighted score for an answer} = \text{SUM } [((\text{answer } \#1) \times (\text{confidence } \#1) \times (AI \text{ specialist } \#1 \text{ weight})) + \ldots ((\text{answer } \#M) \times (\text{confidence } \#M) \times (AI \text{ specialist } \#M \text{ weight}))$$

Example: Patient was in a Car Accident

The patient 120 comes in and says "I was in a car accident. I feel dizzy, my leg hurts, and I find it hard to breathe." In this example, a car accident is the context 164 and the set of symptoms 166 are dizzy, leg pain, and difficulty breathing. In an initial assessment, the triage AI 111 may bring in an emergency medicine AI specialist (from the AI specialists 112) into the subset 146 to access the conversation between the doctor 118 and the patient 120. The emergency medicine AI specialist may provide, in the decision support insights 140, various questions for the doctor 118 to ask the patient 120. For example, the questions may include: "Are you having difficulty breathing?", "Do you feel any numbness or tingling in your legs?", "Can you recall what happened before and after the accident?", and so on. The emergency medicine AI specialist may output, to the decision support insights 140, differentials such as punctured lung, concussion, fractured limb, or any combination thereof.

The triage AI 111 may determine, based on a set of (one or more) trigger words in the conversation, that the conversation has shifted to the lung. The triage AI 111 may remove the emergency medicine AI specialist from the subset 146 or keep the emergency medicine AI specialist in the subset 146, depending on the context 164, set of symptoms 166, and conversation. The triage AI 111 may add a pulmonologist AI specialist (from the AI specialists 112) into the subset 146 to access the conversation between the doctor 118 and the patient 120. The pulmonologist AI specialist may provide, in the decision support insights 140, various questions for the doctor 118 to ask the patient 120. For example, the questions may include: "Are you having chest pain or coughing up blood?", "Do you experience difficultly when taking a deep breath?", "Do you experience a shar pain when you breath in deeply?" and so on. The emergency medicine AI specialist may output, to the decision support insights 140, differentials such as punctured lung, rib fracture, pneumothorax, or any combination thereof.

The triage AI 111 may determine, based on a set of one or more trigger words in the conversation, that the conversation has shifted to the head. The triage AI 111 may remove the pulmonologist AI specialist from the subset 146 or keep the pulmonologist AI specialist in the subset 146, depending on the context 164, set of symptoms 166 (where a set is one or more elements), and conversation. The triage AI 111 may add a neurologist AI specialist (from the AI specialists 112) into the subset 146 to access the conversation between the doctor 118 and the patient 120. The neurologist AI specialist may provide, in the decision support insights 140, various questions for the doctor 118 to ask the patient 120. For example, the questions may include: "Are you experiencing confusion, memory loss, or nausea?", "Are you feeling dizzy or experiencing a sensitivity to light?", "Did you vomit after the accident occurred?" and so on. The pulmonologist AI specialist may output, to the decision support insights 140, differentials such as concussion, intracranial bleed, brain contusion, or any combination thereof.

The triage AI 111 may determine, based on a set of (one or more) trigger words in the conversation, that the conversation has shifted to the legs. The triage AI 111 may remove the neurologist AI specialist from the subset 146 or keep the neurologist AI specialist in the subset 146, depending on the context 164, set of symptoms 166, and conversation. The triage AI 111 may add an orthopedic AI specialist (from the AI specialists 112) into the subset 146 to access the conversation between the doctor 118 and the patient 120. The orthopedic AI specialist may provide, in the decision support insights 140, various questions for the doctor 118 to ask the patient 120. For example, the questions may include: "Is the pain localized or is the pain radiating to other parts of your leg?", "Can you move your toes or does your leg feel numb?", "Do you recall experiencing a specific impact or twisting of the leg?" and so on. The orthopedic AI specialist may output, to the decision support insights 140, differentials such as fractured femur, ligament damage, contusion, or any combination thereof.

The computing device 102 displays the various elements, including the decision support insights 140, in a graphical user interface (GUI). The insights (output 126) provided by the AI specialists 112 in the subset 146 that are listening to the conversation between the doctor 118 and the patient are displayed using different graphical elements, compared to other information displayed by the GUI. For example, the insights provided by the AI specialists may be displayed using a different font, a different font size, a different font color, highlighting, bold, italics, or any combination therefore compared to other information displayed by the GUI.

The consensus AI 148 may review the opinions of the specialists (emergency medicine specialist, pulmonologist, neurologist, orthopedic specialist) and ask questions, such as "Does your breathing or leg pain worsen when you move?", "Are any symptoms connected, such as lightheadedness and pain when breathing?", and so on. The consensus AI 148 may output, to the decision support insights 140, differentials such as compounded trauma, delayed pneumothorax, neurological/musculoskeletal impact, or any combination thereof.

Thus, an interface may capture a portion (one or more turns) of a conversation between a doctor and a patient and send the captured portion, as audio data, transcribed text data, or both to one or more AIs. A triage AI analyzes the conversation and brings in to listen to the conversation, based on the conversation and the patient's symptoms, various AI specialists. Each AI specialist provides decision support insights, such as suggested questions for the doctor to ask the patient, suggestions for one or more tests to be given to the patient, suggestions for one or more referrals to a specialist, possible contraindications, differential diagnosis, suggested diagnoses, suggested prescriptions, and other similar AI-derived insights. These decision support insights are designed to support the doctor during the doctor's conversation with the patient by making the doctor aware of these insights based on conversation, the patient's medical history, and current medical knowledge.

Figure 2:
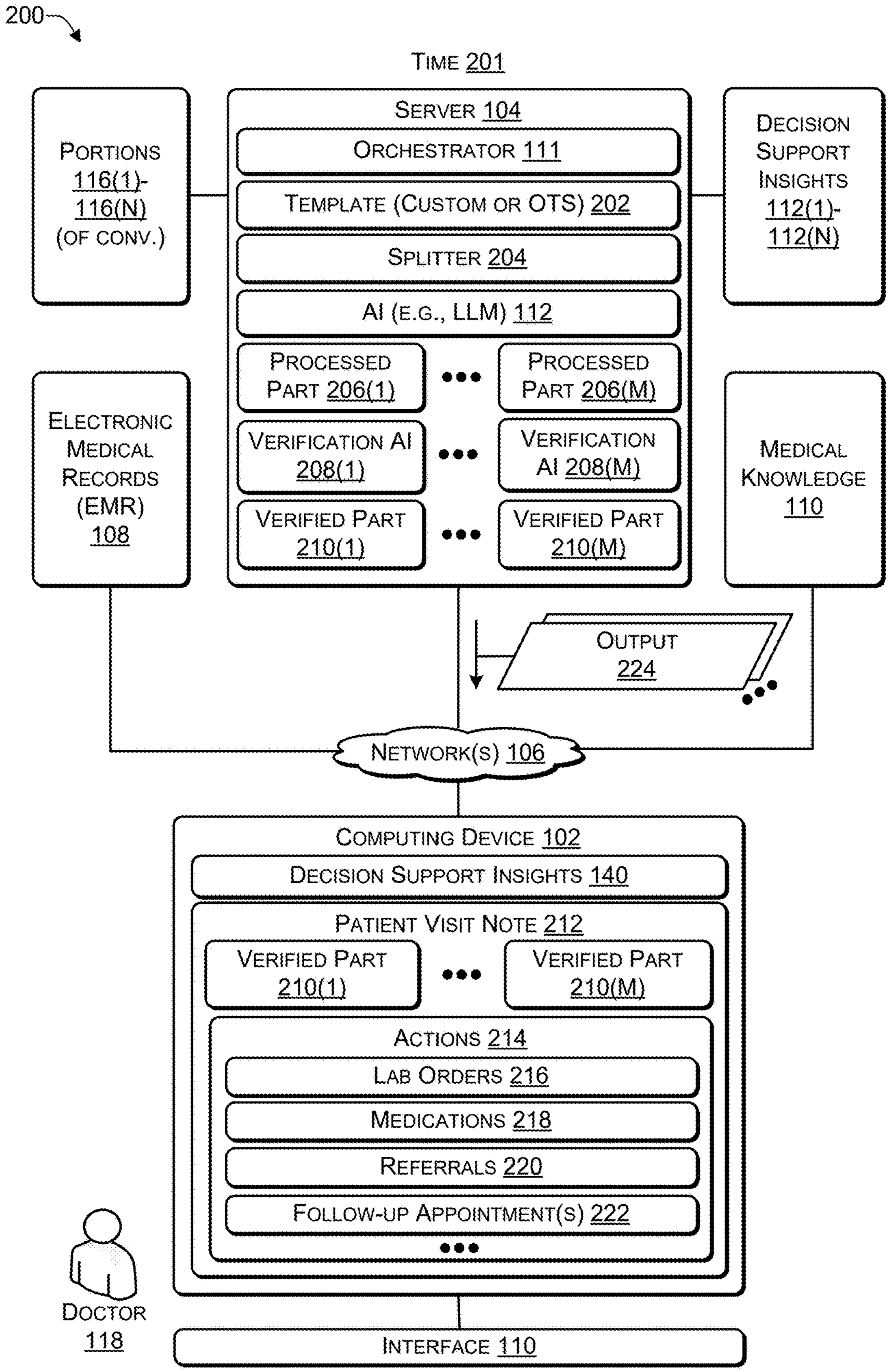
FIG. 2 is a block diagram of a system illustrating an artificial intelligence (AI) architecture creating a note (e.g., Subjective, Objective, Assessment, and Plan (SOAP) note) after a doctor has concluded a conversation with a patient, according to some implementations.

FIG. 2 is a block diagram of a system 200 illustrating an artificial intelligence (AI) architecture creating a note (e.g., a Subjective, Objective, Assessment, and Plan (SOAP) note or similar) after a doctor has concluded a conversation with a patient, according to some implementations. FIG. 2 illustrates what occurs after the AI 112 determines that the conversation between the doctor 118 and the patient 120 has ended, at a time 201. The time 201 occurs after the AI 112 determines that at least one of the doctor 118 or the patient 120 has left the room (e.g., examination room) or is no longer participating in a telehealth call and occurs after the time 122(N) of FIG. 1. The conversation between the doctor 118 and the patient 120, including portions 116(1) to 116(N), and the decision support insights 140(1) to 140(N), generated by the AI 112 in response to the conversation, may be used by the AI 112 to generate a patient visit note 212.

The triage agent 111 may select a template 202 specified by the doctor 118. The template 202 may be an off-the-shelf (OTS) template selected by the doctor 118 or a custom template designed by the doctor 118. The triage agent 111 may instruct a splitter module 204 to categorize the conversation portions 116 and the decision support insights 140 based on the template 202 to create processed parts 206(1) to 206(M) (M>0, typically 4 to 6). For example, when creating a SOAP note, the conversation portions 116 and the decision support insights 140 may be placed by the splitter 204 into 4 categories (Subjective, Objective, Assessment, and Plan).

Each category of the processed parts 206 may have a corresponding verification AI 208. For example, the processed part 206(1) may be verified by the verification AI 208(1) and the processed part 206(M) may be verified by the verification AI 208(M). Each of the verification AI 208 may be trained to perform verification of a particular portion of the patient visit note 212 to enable the verification to occur quickly (in real-time). The verification AI 208(1) to 208(M) may verify the processed parts 206(1) to 206(M) to produce verified parts 210(1) to 210(M), respectively. The verified parts 210(1) to 210(M) may be included in output 232 to the computing device 102.

Thus, the portions 116(1) to 116(N) of the conversation and the decision support insights 140(1) to 140(N) may be split into multiple parts 206 (e.g., based on a doctor specified template 202). The multiple parts 206(1) to 206(M) may be generated in parallel using multiple instances of the AI 112. For example, one of the parts 206 may be a history of present illness (HPI). To reduce pollution in individual parts of the note, such as the HPI, each of the verification AI 208 (e.g., LLM) may be trained to perform verification of a particular one of the parts of the patient visit note 212. In this way, the template 202 may be used to split the portions 116 and insights 140 into multiple parts 206, with multiple instances of the AI 112 generating each of the multiple parts 112 in parallel. Individual verification AIs 208 may be used to verify each of the processed parts 206. For example, a particular verification AI 208 may be trained to perform verification of the HPI part (one of the parts 206) of the note 212. Because each verification AI 208 is trained to verify, the note 112 (having multiple parts) can be generated and verified quickly (typically within a few seconds). The verification AI 208 may be able to perform verification much faster than the AI 112 takes to generate each of the processed parts 206. The verification AI 208 may use as input (1) a transcript of the portions 116 of the conversation and (2) the processed part 206 (e.g., HPI) that was generated by the AI 112. For example, a part 206 of the note 212 may include billing codes. The AI 112 generates (predicts) a billing code while the verification AI 208 verifies that the billing code is correct, by determining if certain words associated with the billing code are mentioned in the transcript of the portions 116 of the conversation. The verification AI 208 are low latency but improve the quality of each part of the note 212. The number of parts of the note 212 may vary based on the doctor. For example, in some cases, note generation may be split into 5 parts: (1) generate HPI, (2) generate subjective exam, (3) generate assessment, (4) generate plan, and (5) generate patient instructions. Without the AI 112, the doctor 118 may manually type all of this in to the computing device 102, typically taking at least several minutes per patient.

In some cases, the AI 112 and the splitter 204 may perform dynamic splitting. The AI 112 may review the selected template 202 and dynamically determine how to split the template 202 into multiple parts 206. The AI 112 uses the splitter 204 to dynamically split the template 202 to create multiple parts 206 and uses the multiple verification AI 208 to verify each of the parts 206, and then merges the verified parts 210 to create the note 212. The computing device 102 may receive the output 232 from the server 104 and create the patient visit note 212 and a set of selectable actions 214. The patient visit note 212 may include the verified data 210(1) to 210(M) organized according to the template 202.

The actions 214 may include suggested actions derived from the decision support insights 140(1) to 140(N), such as lab orders 216, medications 218, referrals 220, follow-up appointments 222, and other actions. The actions 214 may be selectable to enable the doctor 118 to select which of the actions 214 the doctor 118 desires to be performed. For example, the doctor 118 may select (1) a lab order to be sent to the lab for a comprehensive metabolic panel (CMP), (2) a new medication or a refill for an existing medication be sent to a pharmacy associated with the patient 120, (3) a referral letter be sent referring the patient 120 to a particular specialist (cardiologist, gastroenterologist, endocrinologist, or the like), schedule a follow-up appointment in six months, and so on. After selecting one or more of the actions 214 the doctor 118 can initiate the selected actions using the computing device 102. In this way, the doctor 118 avoids manually reviewing the doctor's notes to determine what further actions to take. Instead, the AI 112 provides a list of possible actions 214 derived from the decision support insights 140(1) to 140(N), enabling the doctor 118 to perform one or more of the actions 214 simply by selecting one or more of the actions 214 and instructing the computing device 102 to perform the selected actions.

Thus, after an AI determines that a conversation between a patient in a doctor has ended, the AI may create a patient visit note that summarizes the patient visit. For example, the note may be in the form of a SOAP or similar note. In addition, the AI may generate a set of actions, based on the decision support insights generated during the visit, to enable the doctor to quickly select and initiate one or more of the actions. In this way, the AI is able to save the doctor a significant amount of time because the doctor does not manually create the patient visit note and does not manually enter and initiate one or more actions.

Figure 3:
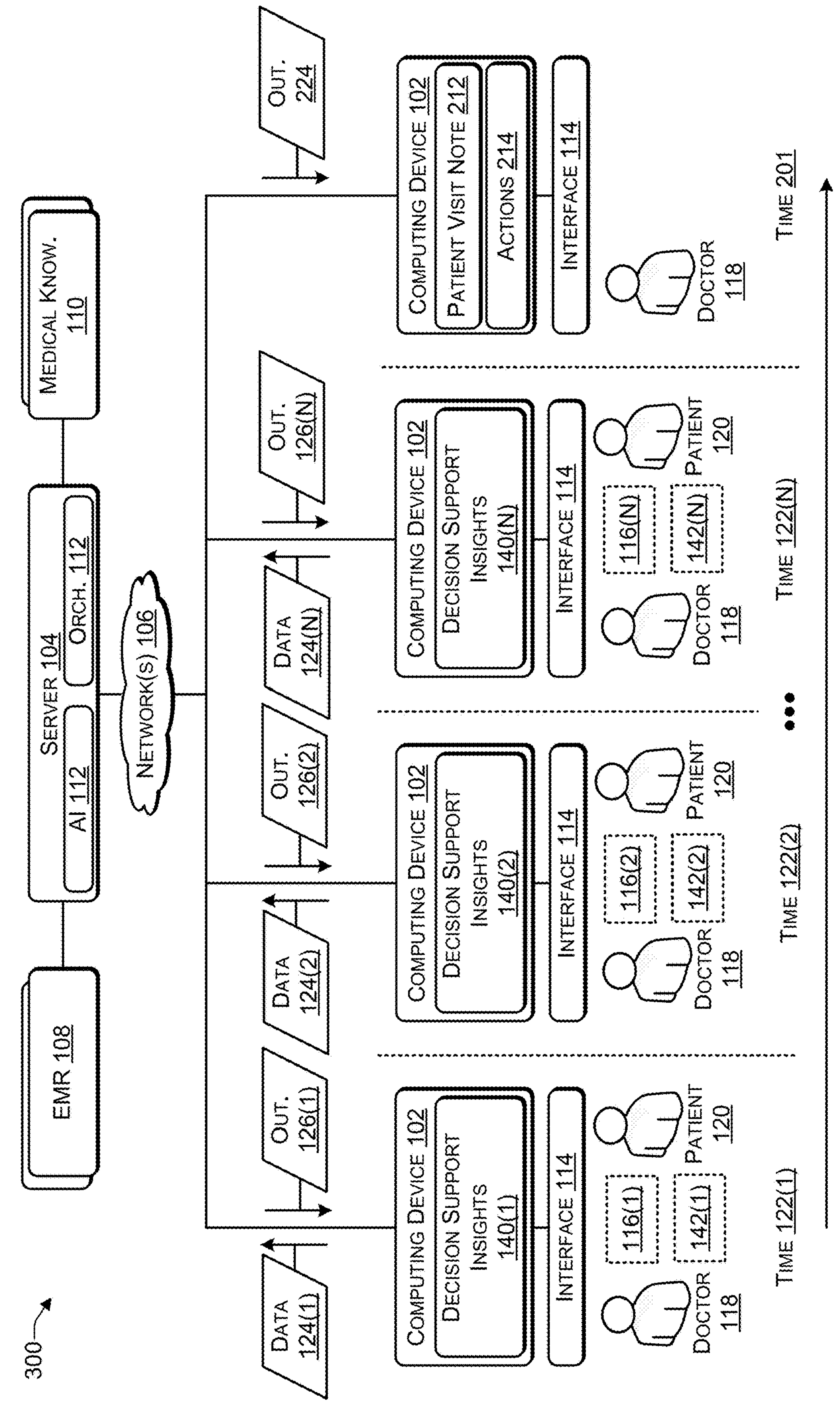
FIG. 3 is a block diagram of a timeline illustrating an artificial intelligence (AI) providing decision support insights to a doctor, according to some implementations.

FIG. 3 is a block diagram of a timeline 300 illustrating an artificial intelligence (AI) providing decision support insights to a doctor, according to some implementations. The timeline 300 illustrates when different events occur. For example, at the time 122(1), the patient 120 initially meets with the doctor 118. The computing device 102 displays the initial decision support insights 140(1). The computing device 102 gathers and sends the biometrics 142(1) (if available) and the portion 116(1) of the conversation between the doctor 118 and the patient 120 to the AI 112. At the time 122(2), the patient 120 continues the visit with the doctor 118. The computing device 102 displays the decision support insights 140(2) generated by the AI 112 and based on the portion 116(1) of the conversation, the EMR 108, and the medical knowledge 110. The computing device 102 gathers and sends the biometrics 142(2) (if available) and the portion 116(2) of the conversation between the doctor 118 and the patient 120 to the AI 112. The computing device 102 displays the decision support insights 140(N) generated by the AI 112 and based on the portion 116(N−1) of the conversation, the EMR 108, and the medical knowledge 110. The computing device 102 gathers and sends the biometrics 142(N) (if available) and the portion 116(N) of the conversation between the doctor 118 and the patient 120 to the AI 112. In some cases, the AI 112 may determine that the conversation between the doctor 118 and the patient 120 has ended based on the portion 116(N). For example, the portion 116(N) may include the doctor 118 and/or the patient 120 verbally indicating (e.g., "Goodbye", "See you in 6 months", or the like) that the conversation has ended. After the AI 112 determines that the conversation has ended or in response to a request from the doctor 118, the AI 112 may generate the patient visit note 212 and one or more follow-up actions 214.

In the flow diagram of FIGS. 4, 5, 6, 7, and 8, each block represents one or more operations that can be implemented in hardware, software, or a combination thereof. In the context of software, the blocks represent computer-executable instructions that, when executed by one or more processors, cause the processors to perform the recited operations. Generally, computer-executable instructions include routines, programs, objects, modules, components, data structures, and the like that perform particular functions or implement particular abstract data types. The order in which the blocks are described is not intended to be construed as a limitation, and any number of the described operations can be combined in any order and/or in parallel to implement the processes. For discussion purposes, the processes 400, 500, 600, 700, and 800 are described with reference to FIGS. 1, 2, and 3 as described above, although other models, frameworks, systems and environments may be used to implement these processes.

Figure 4:
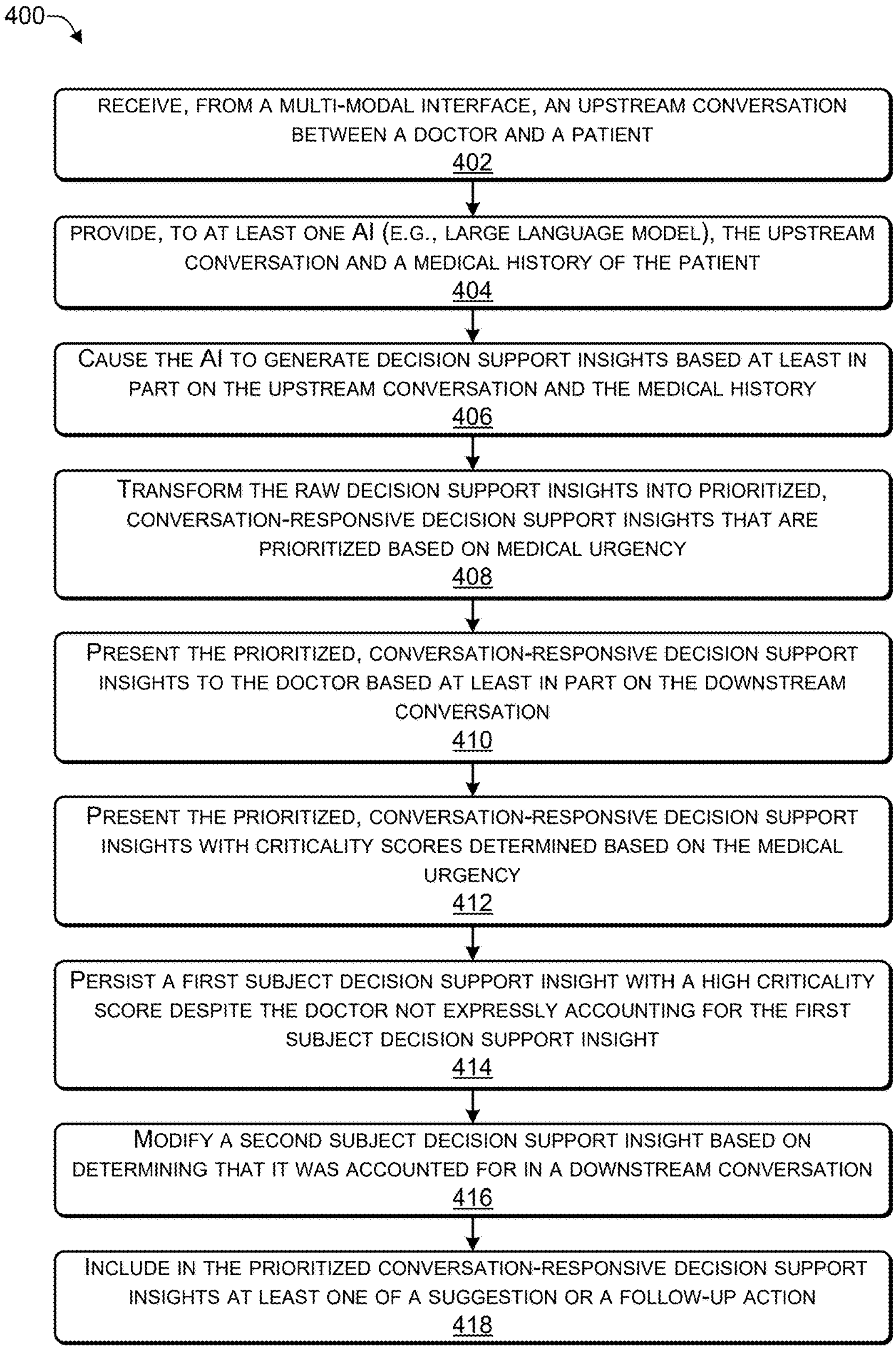
FIG. 4 is a flowchart of a process that includes causing an artificial intelligence (AI) to generate decision support insights, according to some implementations.

FIG. 4 is a flowchart of a process 400 that includes causing an artificial intelligence (AI) to generate decision support insights, according to some implementations. The process 400 may be performed by one or more components of the server 104 and/or the computing device 102 of FIGS. 1, 2, and 3.

At 402, the process may receive, from a multimodal interface, an upstream conversation between a doctor and a patient. For example, in FIG. 1, the AI 112 may receive, from the interface 114, the portion 116(1) of the upstream conversation between the doctor 118 and the patient 120.

At 404, the process may provide, to at least one AI (such as a large language model), the upstream conversation and a medical history of the patient. At 406, the process may cause the AI to generate decision support insights based at least in part on the upstream conversation and the medical history. For example, in FIG. 1, AI 112 (e.g., a large language model) may receive the upstream portion 116(1) of the conversation and access a medical history of the patient using the EMR 108. The AI 112 may generate decision support insights 140 based at least in part on the upstream portion 116(1) of the conversation and the medical history from the EMR 108.

At 408, the process may transform the raw decision support insights into prioritized conversation responsive decision support insights that are prioritized based on medical urgency. At 410, the process may present the prioritized, conversation responsive decision support insights to the doctor based at least in part on the downstream conversation. At 412, the process may present individual ones of the prioritized, conversation responsive decision support insights with an associated criticality score that is determined based on the medical urgency. For example, in FIG. 1, the post processing 128 (located either at the computing device 102 or at the server 104) may transform the output 126(N) (e.g., raw decision support insights) into prioritized conversation responsive decision support insights 140 that are prioritized (by the prioritization module 134) based on medical urgency. The prioritized, conversation responsive decision support insights 140(N) are presented to the doctor 118 based at least in part on the downstream portion 116(N) of the conversation. Individual prioritized, conversation responsive decision support insights 140(N) may be presented by the computing device 102 with an associated criticality score that is determined based on the medical urgency.

At 414, the process may persist a first subject decision support insight with a high criticality score despite the doctor not expressly accounting for the first subject decision support insight. For example, in FIG. 3, the decision support insights 140(2) may include an insight with a high criticality score. If the AI 112 determines, based at least in part on the portion 116(2) of the conversation, that the doctor has not expressly accounted for the insight with the high criticality score, the AI 112 may persist the insight with the high criticality score in one or more subsequent decision support insights 140(N), e.g., until the doctor expressly accounts for the insight with the high criticality score.

At 416, the process may modify a second subject decision support insight based on determining that it was accounted for in the downstream conversation. For example, in FIG. 1, the AI 112 may include an instruction in the adjustments 132 to modify a second subject decision support insight in the decision support insights 140 based on determining that it was accounted for in the downstream portion 116(N) of the conversation. To illustrate, the AI 112 may determine that one of the suggestions 138 to ask the patient a particular question can be removed because either the doctor 118 asked the question or the patient 120 volunteered information answering the question. To illustrate, if the doctor 118 determines that the patient 120 is likely suffering from high blood pressure and is considering prescribing a diuretic, the AI 112 may provide in the suggestions 138 that the doctor 118 ask the patient 120 if the patient has previously suffered from gout. Before or while the suggestions 138 are being displayed by the computing device 102, the doctor 118 may ask the patient 120 whether the patient 120 has previously suffered from gout. Alternately, before or while the suggestions 138 are being displayed by the computing device 102, the patient 120 may volunteer that the patient 120 has previously suffered from gout. In either case, the AI 112 determines that the suggestion to the doctor 118 to ask the patient 120 the question (whether the patient 120 has previously suffered from gout) is no longer applicable and includes an instruction in the adjustments 132 to remove that particular question from the suggestions 138 or the decision support insights 140(N).

At 418, the process may include in the prioritized conversation responsive decision support insights at least one of a suggestion or a follow-up action. For example, in FIG. 1, the suggestions 138 in the decision support insights 140(N) may include questions for the doctor 118 to ask the patient 120, suggestions for one or more tests for the patient 120, suggestions for one or more referrals, suggested diagnoses, suggested prescriptions, and other insights derived from the portion 116 of the conversation, the EMR 108, and the medical knowledge databases 110.

Thus, an AI may receive a portion of a conversation between a doctor and a patient and generate one or more decision support insights based on the portion of the conversation and a medical history of the patient. The rod this decision support insights may be prioritized based on medical urgency and presented accordingly. For example, urgent decision support insights may be presented in a larger font, in a different font, in a bolder font, in a different colored font, or the like to enable the doctor to easily identify the more critical insights from other insights. The AI may persist, in a subsequent set of decision support insights, a critical insight that the doctor does not expressly account for. If the AI determines that a particular issue identified in an insight has either been raised by the doctor or addressed by the patient, then the AI may modify the insight to indicate that it has been accounted for. The decision support insights may include a suggestion or a follow-up action. In this way, the AI is able to augment the doctor's insights by suggesting alternatives that the doctor may not normally consider and reminding the doctor of insights that normally occur to the doctor. Thus, even if the doctor forgets to ask a question or perform an action that the doctor normally does, the AI is able to remind the doctor of the question or action to be performed.

Figure 5:
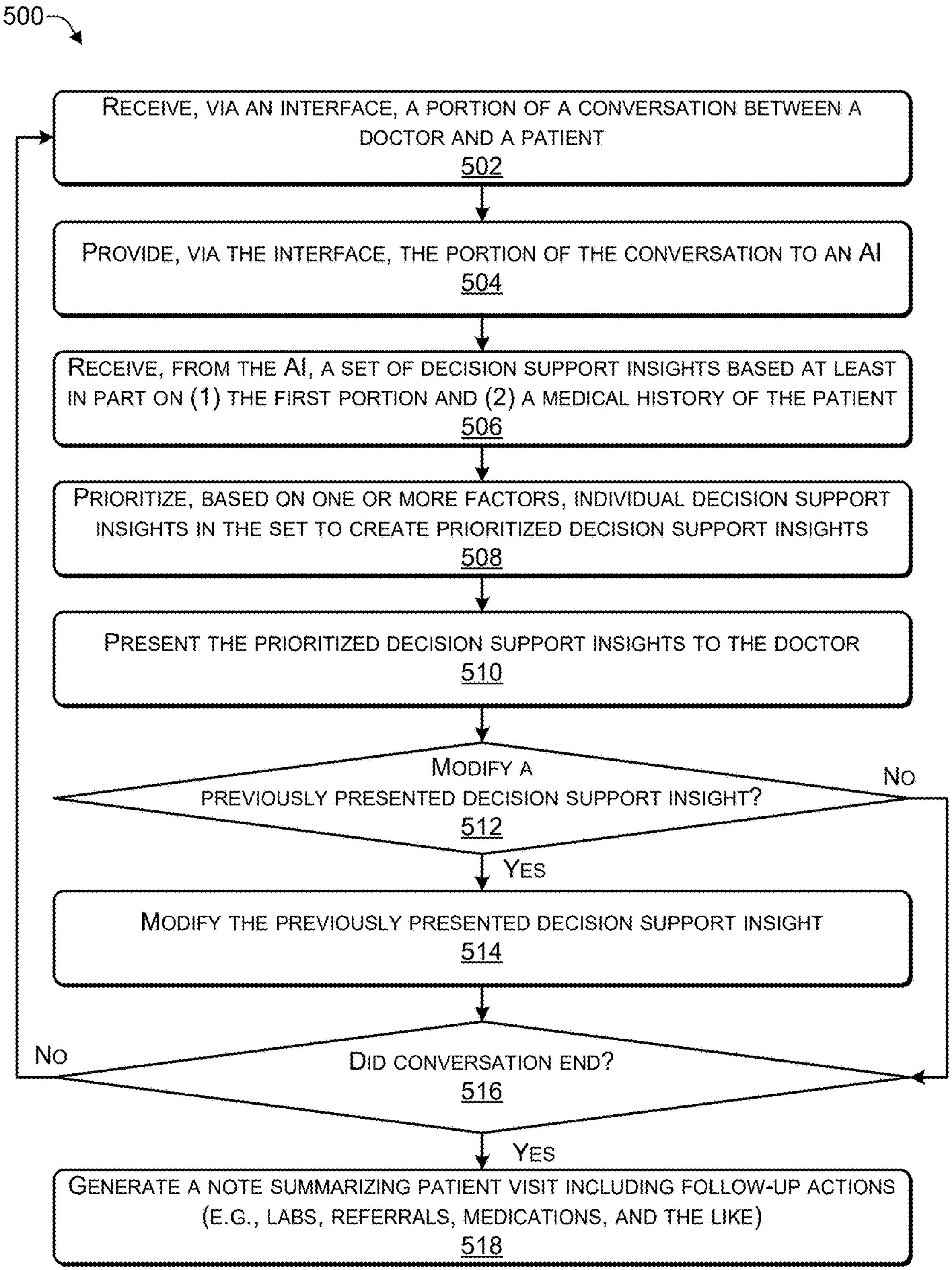
FIG. 5 is a flowchart of a process that includes presenting prioritized decision support insights to a doctor, according to some implementations.

FIG. 5 is a flowchart of a process 500 that includes presenting prioritized decision support insights to a doctor, according to some implementations. The process 500 may be performed by the interface 114 or one or more components of the computing device 102 of FIGS. 1, 2, and 3.

At 502, the process may receive, via an interface, a portion of a conversation between a doctor and a patient. At 504, the process may provide, via the interface, the portion of the conversation to an AI. For example, in FIG. 1, the interface 114 may receive the portion 116(1) of the conversation between the doctor 118 and the patient 120. The interface 114 may provide the portion 116(1) of the conversation, as audio data, transcribed text data, or a combination of both, to the server 104 for the AI 112 to process. For example, if portions of the audio data could not be transcribed with a particular degree of confidence (e.g., 90%, 95% or the like), then audio data may be included with a transcription of the audio data.

At 506, the process may receive, from the AI, a set of decision support insights based at least part on the first portion of the conversation and a medical history of the patient. At 508, the process may prioritize, based on one or more factors, individual decision support insights in the set of decision-support insights to create prioritized decision support insights. At 510, the process may present the prioritized decision support insights to the doctor. For example, in FIG. 1, the computing device 102 may receive the output 126 from the server 104 that the AI 112 has determined based on the portion 116(1) of the conversation and a medical history of the patient 120 derived from the electronic medical records 108. The computing device 102 may perform post processing 128 of the output 126(N), including prioritizing the decision support insights 140(N), based on one or more factors, such as based on a criticality score. In some cases, the criticality score may be determined based on medical urgency.

At 512, the process may determine whether to modify a previously presented decision-support insight. If the process determines, at 512, that "yes" a previously presented decision-support insight is to be modified, then the process may proceed to 514, where the previously presented decision-support insight is modified, and the process proceeds to 516. If the process determines, at 512, that "no" the previously presented decision-support insight is not to be modified, then the process proceeds to 516. For example, in FIG. 1, the post processing 128 may determine whether a previously presented decision-support insight (of the insights 140) is to be modified. For example, the adjustments 132 may include instructions on whether to modify one or more of the decision support insights 140(N). To illustrate, if the doctor has not expressly acknowledged an important or critical decision support insight, then the adjustments 132 may include displaying the decision-support insight in such a way as to indicate the importance or criticality of the insight. As another illustration, if a decision support insight was to obtain particular information from the patient 120 and either the doctor 118 asked a question to obtain the particular information or the patient 120 volunteered the particular information, then the adjustments 132 may include an instruction to remove the decision-support insight to obtain the particular information from the displayed decision support insights 140. If the adjustments 132 is an empty set and there are no instructions to make adjustments, then no adjustments are made to the decision support insights 140 (N).

At 516, the process determines whether the conversation has ended. If the process determines, at 516, that "no" the conversation has not ended, then the process proceeds back to 502 to receive a subsequent portion of the conversation between the doctor and the patient via the interface. For example, in FIG. 3, the interface 114 may determine whether the conversation between the doctor 118 and the patient 120 has ended. If a determination is made that the conversation has not ended, then the interface 114 may receive a subsequent portion 116 of the conversation between the doctor 118 and the patient 120.

If the process determines, at 516, that "yes" the conversation has ended, then the process generates a note summarizing the patient visit, including follow-up actions (e.g., labs, referrals, medications, and the like), at 518. For example, in FIG. 2, if a determination is made that the conversation between the doctor 118 and the patient 120 has ended, then the process generates patient visit note 212 summarizing the patient visit and suggested follow-up actions 214 (e.g., labs, referrals, medications, and the like).

Thus, a portion of a conversation (e.g., that includes one or more turns) is captured by an interface and sent to an AI hosted by a server. The conversation may be sent as audio data, as transcribed text data, or a combination of both. The AI may access the patient's medical records and in some cases, access current medical knowledge databases, to generate decision support insights for the doctor. The decision support insights may be prioritized prior to being presented to the doctor. For example, the decision-support insight may be prioritized based on medical urgency relative to the patient or another factor. In some cases, the AI may provide instructions to modify a previously presented decision-support insight by persisting an insight that the doctor has not expressly acknowledged or by modifying or removing an insight associated with particular information. For example, if the AI has made a suggestion to the doctor to request particular information from the patient and the doctor has either asked for the particular information or the patient has volunteered the particular information, then the AI may remove the suggestion from the decision support insights. If the AI has made a suggestion to the doctor to request particular information from the patient and part of the particular information has been obtained, then the AI may modify the suggestion to obtain the remaining portion of the particular information.

Figure 6:
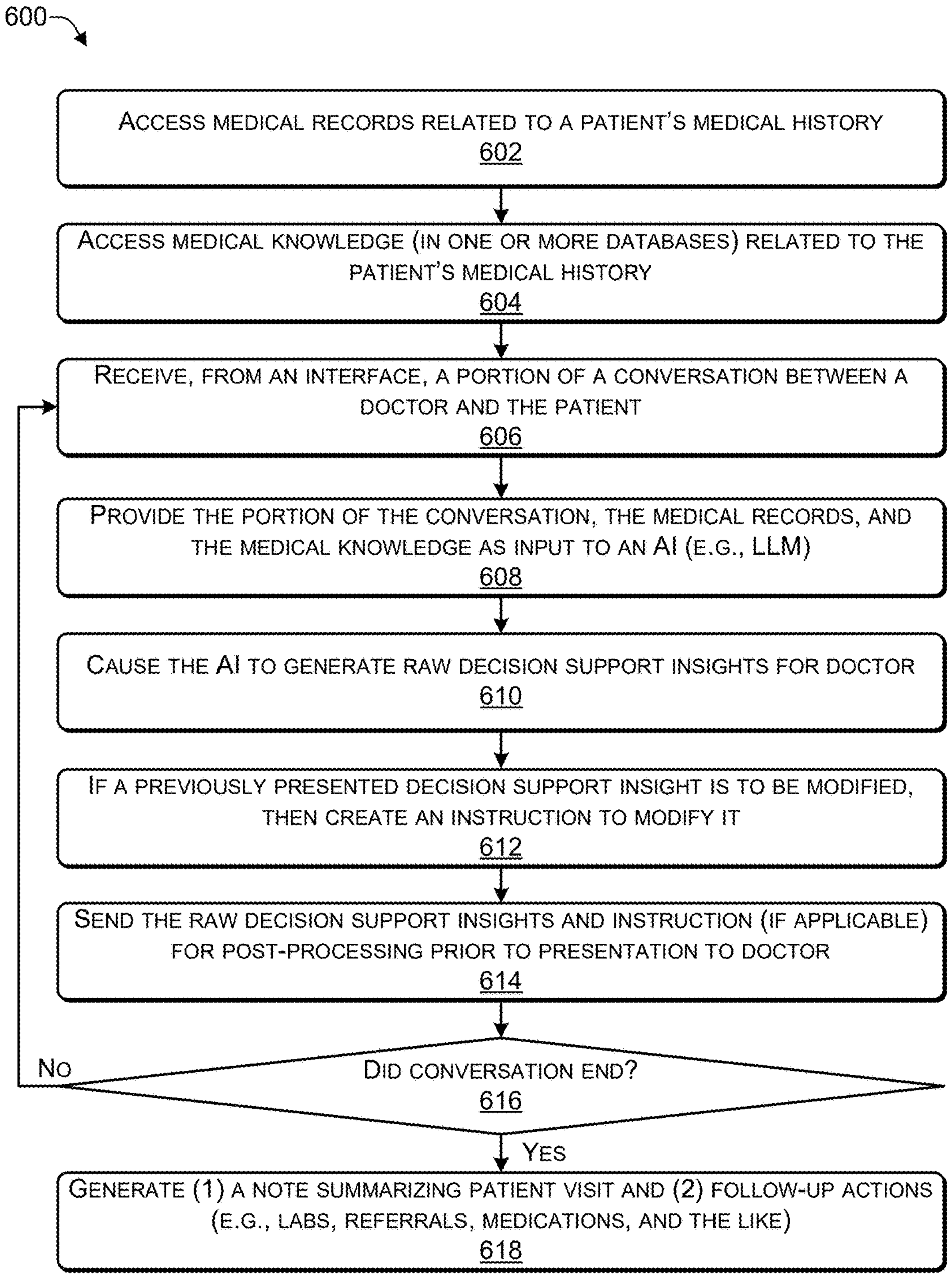
FIG. 6 is a flowchart of a process that includes sending raw decision support insights to an interface for post-processing prior to presentation to a doctor, according to some implementations.

FIG. 6 is a flowchart of a process 600 that includes sending raw decision support insights to an interface for post-processing prior to presentation to a doctor, according to some implementations. The process 600 may be performed by one or more components of the server 104 of FIGS. 1, 2, and 3.

At 602, the process may access medical records related to a patient's medical history. At 604, the process may access medical knowledge (in one or more databases) related to the patient's medical history. At 606, the process may receive, from an interface, a portion of a conversation between a doctor and the patient. At 608, the process may provide the portion of the conversation, the medical records, and the medical knowledge as input to an AI (e.g., LLM). At 610, the process may cause the AI to generate raw decision support insights for the doctor. At 612, if a previously presented decision-support insight is to be modified in the process creates an instruction to modify it. At 614, the process sends the raw decision support insights and instruction (if applicable) to the interface for postprocessing prior to presentation to a doctor. For example, in FIG. 1, the triage agent 111 may access electronic medical records 108 related to a medical history of the patient 120. The triage agent 111 may access medical knowledge (in one or more databases 110) related to the patient's medical history. The triage agent 111 may receive the portion 116(1) of a conversation between the doctor 118 and the patient 120 as audio data, transcribed text data, or a combination of both. The triage agent 111 may provide the portion 116(1) of the conversation, the relevant medical records 108, and the relevant medical knowledge 110 as input to the AI 112 (e.g., LLM). The AI 112 may generate raw decision support insights in the output 126(N) that are processed and then presented to the doctor 118. For example, the output 126(N) of the AI 112 may be processed using a post processing module 128. While the post processing module 128 is illustrated as being executed by the computing device 102, in some cases, the post processing module 128 may be executed by the server 104 and the processed decision support insights sent as the output 126 (N) to the computing device 102. If a previously presented decision-support insight is to be modified (e.g., persist an unacknowledged insight or modify an insight that has been partially or fully responded to by either the doctor or the patient), then the AI 112 creates an adjustment instruction in the adjustments 132 modify one of the insights.

At 616, the process determines whether the conversation has ended. If the process determines, at 616, that "no" the conversation has not ended, then the process proceeds back to 606 to receive a subsequent portion of a conversation between the doctor and the patient from the interface. If the process determines, at 616 that "yes" the conversation has ended, then the process generates: (1) a note summarizing the patient visit and (2) follow-up actions. For example, in FIG. 3, the process determines whether the conversation between the doctor 118 and the patient 120 has ended. If the process determines, that the conversation has not ended, then the process proceeds to receive a subsequent portion 116 of a conversation between the doctor 118 and the patient 120. If the process determines, that the conversation between the doctor 118 and the patient 120 has ended, then the process generates: (1) the patient visit note 212 summarizing the patient visit and (2) the follow-up actions 214.

Thus, a triage agent may determine that a patient is about to visit a doctor and access medical records related to the patient's medical history. The triage agent may access medical knowledge related to the patient's medical history. The triage agent may receive a portion of a conversation between a doctor and a patient in the form of audio data, transcribed text data, or a combination of both. The triage agent may provide the portion of the conversation along with the patient's medical history and the medical knowledge relevant to the patient's medical history to an AI. The AI may generate raw decision support insights designed to support the doctor. If a previously presented decision-support insight is to be modified then the AI may create an instruction to modify the previously presented decision-support insight. The raw decision support insights and instruction, if applicable, may be sent for post processing prior to presentation to the doctor. The post processing of the raw decision support insights may occur at a server (e.g., where the AI is executing) or at the computing device associated with the doctor. After determining that the conversation between the doctor and patient has ended the process may generate a note summarizing the patient visit and follow-up actions, such as labs, referrals, medications, and the like to enable the doctor to quickly perform the follow-up actions.

Figure 7:
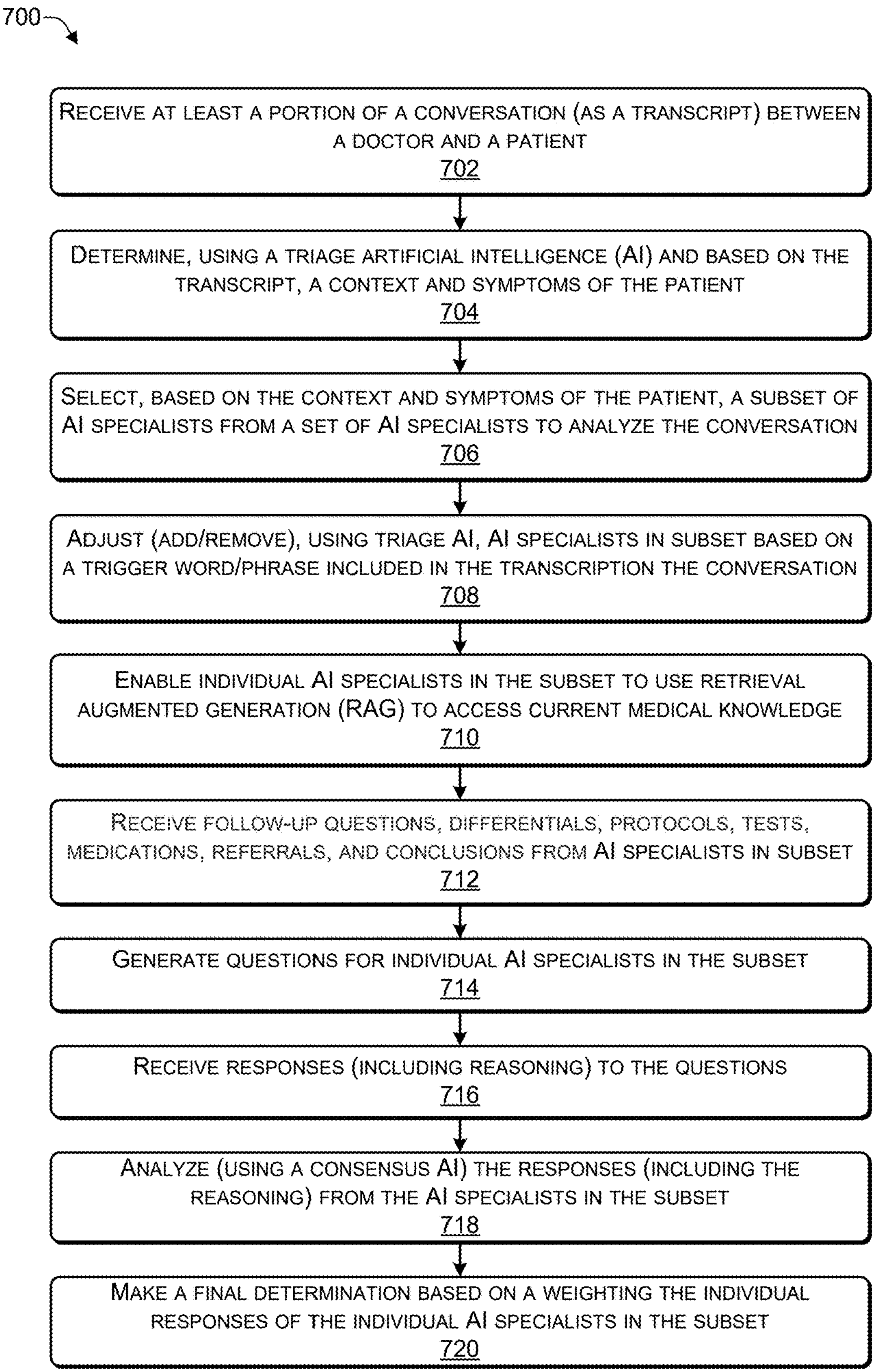
FIG. 7 is a flowchart of a process that includes making a final determination for a patient based on opinions from multiple artificial intelligence (AI) specialists, according to some implementations.

FIG. 7 is a flowchart of a process 700 that includes making a final determination for a patient based on opinions from multiple artificial intelligence (AI) specialists, according to some implementations. The process 700 may be performed by one or more components of the server 104 of FIGS. 1, 2, and 3.

At 702, the process may receive at least a portion of a conversation (in the form of a transcript) between a doctor and a patient. For example, in FIG. 1, the server 104 may receive the data 124 that includes the portion 116 of the conversation between the doctor 118 and the patient 120. The data 124 may include a text-based transcript 152 of the portion 116 of the conversation.

At 704, the process may determine, using a triage artificial intelligence (AI) and based on the transcription, a context, and a set of (one or more) symptoms of the patient. At 706, the process may select, based on the context and the set of (one or more) symptoms of the patient, a subset of AI specialists, from a set of AI specialists, to analyze the conversation. For example, in FIG. 1, the triage AI 111 may determine, based on the transcript 152, the context 164, and the set of symptoms 166 of the patient 120. The triage 111 may select, based on the context 164 and the one or more symptoms 166 of the patient 120, the subset 146 of AI specialists, from the set of AI specialists 112, to analyze the conversation (transcript 152).

At 708, the process may adjust (add/remove) AI specialists, using the triage AI, based on the set of (one or more)

trigger words included in the transcript of the conversation. At 710, the process may enable individual AI specialists in the subset to use retrieval augmented generation (RAG) to access current medical knowledge (via medical knowledge databases). For example, in FIG. 1, the triage AI 111 may adjust (add and/or remove) AI specialists 112 in the subset 146 based on the set of (one or more) trigger words included in the transcript 152 of the conversation. The server 104 may enable individual AI specialists in the subset 146 to use retrieval augmented generation (RAG) to access current medical knowledge in the medical knowledge databases 110.

At 712, the process may receive follow-up questions, differentials, protocols, tests, medications, referrals, and conclusions from AI specialists in the subset. At 714, the process may generate questions for the individual specialists. At 716, the process may receive responses (including reasoning) to the questions. At 718, the process may analyze, using a consensus AI the responses (including the reasoning) from the AI specialists in the subset. At 720, the process may make a final determination based on weighting the individual responses of the individual AI specialists in the subset. For example, in FIG. 1, the triage AI 111 and/or the consensus AI 148 may receive follow-up questions, differentials, protocols, tests, medications, referrals, and conclusions from the AI specialists in the subset 146. The consensus AI 148 may generate questions 156 for the individual AI specialists in the subset 146. The questions 156 may be multiple choice questions, questions that can be answered with a "yes" or "no", or questions that can be answered with one sentence. The consensus AI 148 may receive the answers 158 (including reasoning) to the questions 156 from the individual AI specialists in the subset 146. The consensus AI 148 may analyze the answers 158 (including the reasoning) from the AI specialists in the subset 146. The consensus AI 148 may make a final determination (consensus) based on weighting the individual answers 158 using the confidence level 160. In some cases, the consensus AI 148 may assign a weight to each AI specialist for individual answers 158 and so the weighting may include the answer 158, the confidence level 160, and the weight associated each AI specialist for individual answers 158.

Thus, after a conversation between a doctor and a patient has concluded, an AI may use a template to split up the accumulated conversation and the accumulated decision support insights to create multiple parts. Individual parts of the multiple parts may be verified by individual verification AIs that verify the content of each part of the note based on the relevant portions of the conversation and/or relevant portions of the decision support insights. The verified parts are assembled, based on the template, to create the patient visit note that summarizes the patient's visit. The note may include one or more follow-up actions that the doctor can select to be performed. In this way, the doctor is spared from spending time entering notes and entering and initiating various follow-up actions. This saves the doctor time and allows the doctor to perform tasks, such as seeing more patients, rather than spending time doing paperwork.

Figure 8:
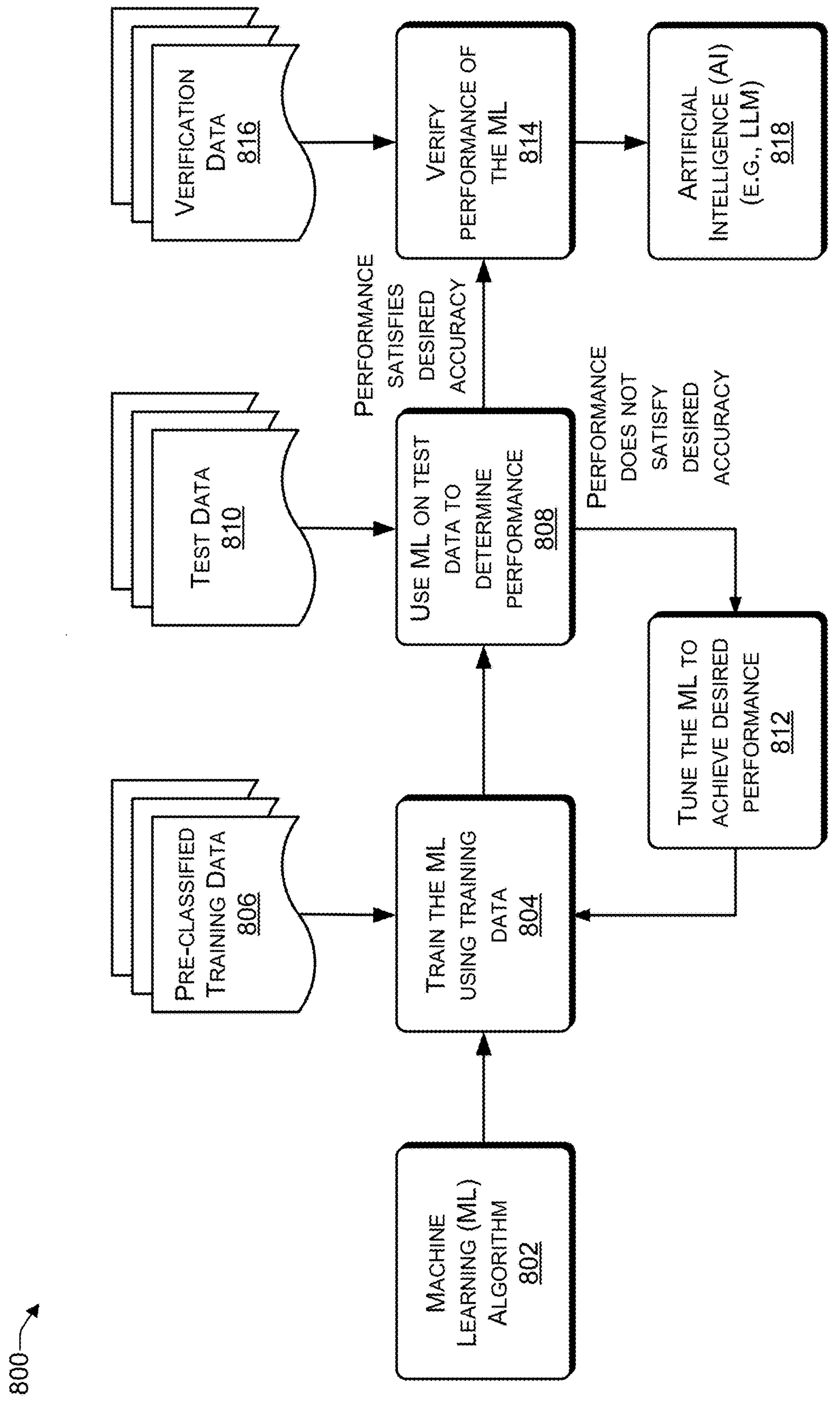
FIG. 8 is a flowchart of a process to train a machine learning algorithm, according to some implementations.

FIG. 8 is a flowchart of a process 800 to train a machine learning algorithm, according to some implementations. For example, the process 800 may be performed to train and create the AI 111, 112, 148, 150 of FIG. 1.

At 802, a machine learning algorithm (e.g., software code) may be created by one or more software designers. At 804, the machine learning algorithm may be trained using pre-classified training data 806. For example, the training data 806 may have been pre-classified by humans, by machine learning, or a combination of both. After the machine learning has been trained using the pre-classified training data 806, the machine learning may be tested, at 808, using test data 810 to determine a performance metric of the machine learning. The performance metric may include, for example, precision, recall, Frechet Inception Distance (FID), or a more complex performance metric. For example, in the case of a classifier, the accuracy of the classification may be determined using the test data 810.

If the performance metric of the machine learning does not satisfy a desired measurement (e.g., 95%, 98%, 99% in the case of accuracy), at 808, then the machine learning code may be tuned, at 812, to achieve the desired performance measurement. For example, at 812, the software designers may modify the machine learning software code to improve the performance of the machine learning algorithm. After the machine learning has been tuned, at 812, the machine learning may be retrained, at 804, using the pre-classified training data 806. In this way, 804, 808, 812 may be repeated until the performance of the machine learning is able to satisfy the desired performance metric. For example, in the case of a classifier, the classifier may be tuned to be able to classify the test data 810 with the desired accuracy.

After determining, at 808, that the performance of the machine learning satisfies the desired performance metric, the process may proceed to 814, where verification data 816 may be used to verify the performance of the machine learning. After the performance of the machine learning is verified, at 814, the machine learning 802, which has been trained to provide a particular level of performance may be used as the artificial intelligence (AI) 111, 112, 148, 150.

Figure 9:
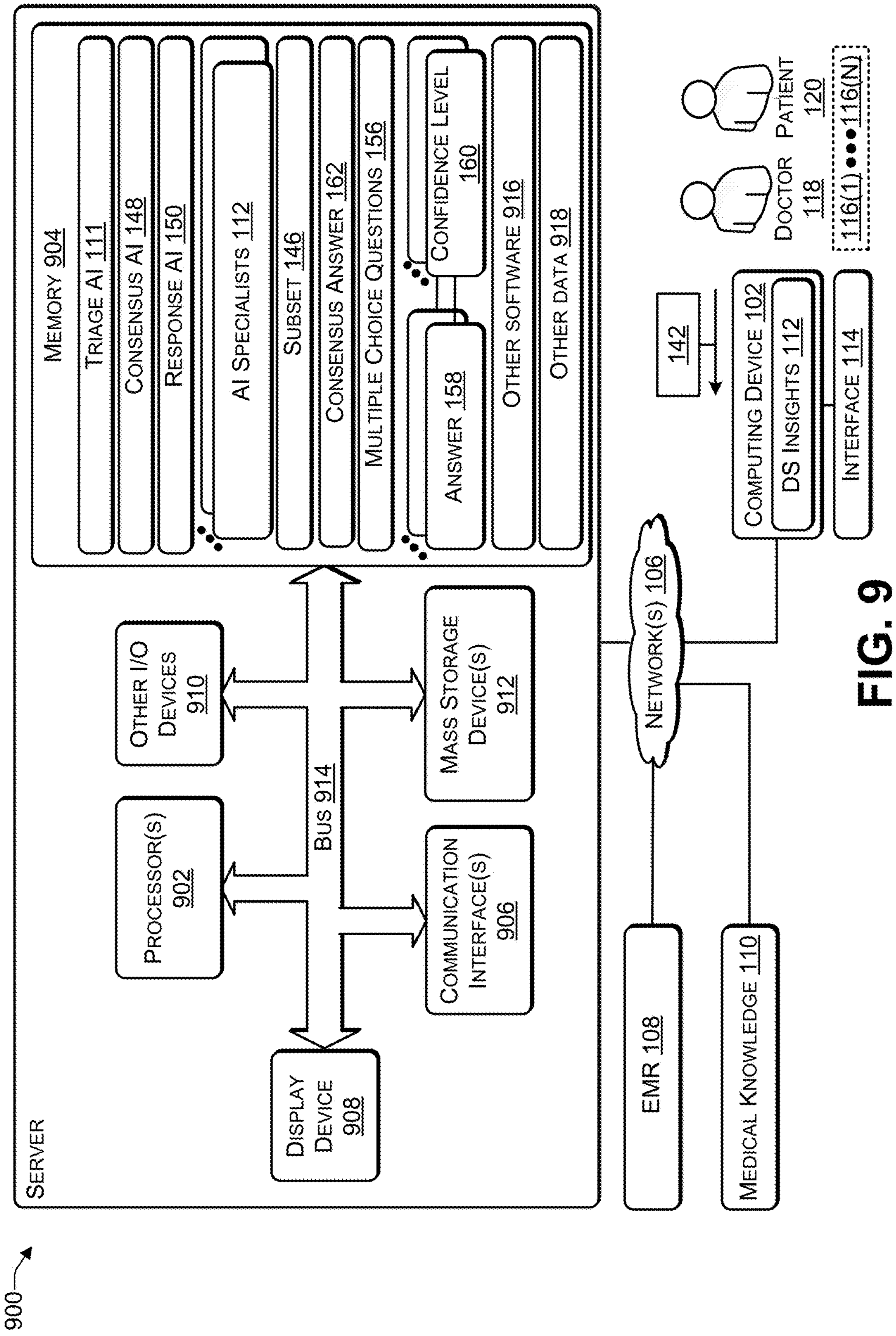
FIG. 9 illustrates an example configuration of a computing device that can be used to implement the systems and techniques described herein.

FIG. 9 illustrates an example configuration of a device 900 that can be used to implement the systems and techniques described herein. For example, the device 900 may be used to implement the computing device 102, the server 104, or the interface 114. For illustration purposes, FIG. 9 shows the device 900 implementing the server 104.

The device 900 may include one or more processors 902 (e.g., central processing unit (CPU), graphics processing unit (GPU), or the like), a memory 904, communication interfaces 906, a display device 908, other input/output (I/O) devices 910 (e.g., keyboard, trackball, and the like), and one or more mass storage devices 912 (e.g., disk drive, solid state disk drive, or the like), configured to communicate with each other, such as via one or more system buses 914 or other suitable connections. While a single system bus 914 is illustrated for ease of understanding, it should be understood that the system bus 914 may include multiple buses, such as a memory device bus, a storage device bus (e.g., serial ATA (SATA) and the like), data buses (e.g., universal serial bus (USB) and the like), video signal buses (e.g., ThunderBolt®, digital video interface (DVI), high definition media interface (HDMI), and the like), power buses, etc.

The processors 902 are one or more hardware devices that may include a single processing unit or a number of processing units, all of which may include single or multiple computing units or multiple cores. The processors 902 may include a graphics processing unit (GPU) that is integrated into the CPU or the GPU may be a separate processor device from the CPU. The processors 902 may be implemented as one or more microprocessors, microcomputers, microcontrollers, digital signal processors, central processing units, graphics processing units, state machines, logic circuitries, and/or any devices that manipulate signals based on operational instructions. Among other capabilities, the processors 902 may be configured to fetch and execute computer-readable instructions stored in the memory 904, mass storage devices 912, or other computer-readable media.

Memory 904 and mass storage devices 912 are examples of computer storage media (e.g., memory storage devices) for storing instructions that can be executed by the processors 902 to perform the various functions described herein. For example, memory 904 may include both volatile memory and non-volatile memory (e.g., random access memory (RAM), read only memory (ROM), or the like) devices. Further, mass storage devices 912 may include hard disk drives, solid-state drives, removable media, including external and removable drives, memory cards, flash memory, floppy disks, optical disks (e.g., compact disc (CD), digital versatile disc (DVD), a storage array, a network attached storage (NAS), a storage area network (SAN), or the like. Both memory 904 and mass storage devices 912 may be collectively referred to as memory or computer storage media herein and may be any type of non-transitory media capable of storing computer-readable, processor-executable program instructions as computer program code that can be executed by the processors 902 as a particular machine configured for carrying out the operations and functions described in the implementations herein.

The device 900 may include one or more communication interfaces 906 for exchanging data via the network 90. The communication interfaces 906 can facilitate communications within a wide variety of networks and protocol types, including wired networks (e.g., Ethernet, Data Over Cable Service Interface Specification (DOCSIS), digital subscriber line (DSL), Fiber, universal serial bus (USB) etc.) and wireless networks (e.g., wireless local area network (WLAN), global system for mobile (GSM), code division multiple access (CDMA), 802.11, Bluetooth, Wireless USB, ZigBee, cellular, satellite, etc.), the Internet and the like. Communication interfaces 906 can also provide communication with external storage, such as a storage array, network attached storage, storage area network, cloud storage, or the like.

The display device 908 may be used for displaying content (e.g., information and images) to users. Other I/O devices 910 may be devices that receive various inputs from a user and provide various outputs to the user, and may include a keyboard, a touchpad, a mouse, a gaming controller (e.g., joystick, steering controller, accelerator pedal, brake pedal controller, virtual reality (VR) headset, VR glove, or the like), a printer, audio input/output devices, and so forth.

The computer storage media, such as memory 904 and mass storage devices 912, may be used to store any of the software and data described herein as well as other software 916 and other data 918.

Figure 10:
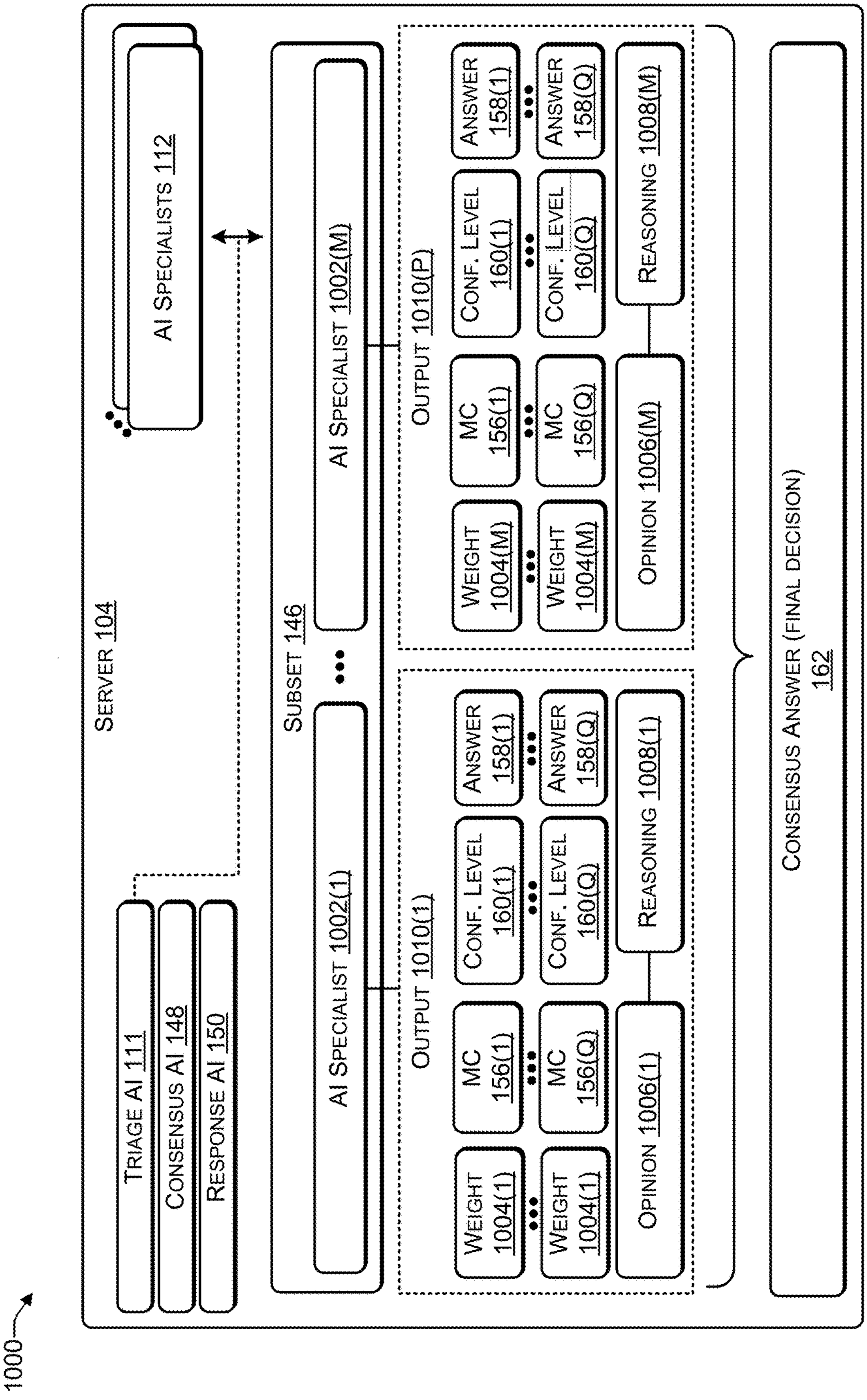
FIG. 10 is a block diagram of a system illustrating determining a consensus answer from multiple artificial intelligence (AI) specialists, according to some implementations.

FIG. 10 is a block diagram of a system 1000 illustrating determining a consensus answer from multiple artificial intelligence (AI) specialists, according to some implementations.

During the conversation, the triage AI 111 examines the content of the portion 116 of the conversation and selects a subset 146 of one or more AI specialists 112 to listen to the conversation and provide insights to the doctor 118. For example, the subset 146 may include AI specialists 1002(1) to 1002(M) (M>0). Typically, the triage 111 may select one to three AI specialists 112 for inclusion in the subset 146 at any given point in time. Of course, more than three specialists may be included in the subset 146 based on the patient's symptoms. Each AI specialist 112 is trained using a particular body of knowledge in their specialty. During the conversation, the triage AI 111 may switch the AI specialists 112 in and out of the subset 146, depending on what is being discussed. Some AI specialists 112 may be present during the entire conversation while others may be brought in and out of the subset 146 that has access to the conversation. For example, if a particular AI specialist 112 is no longer relevant to the context 164, then the particular specialist may be taken out and another specialist brought in. To illustrate, when topic #1 is being discussed, the triage AI 111 detects a set of (one or more) words associated with topic #1 in the portion 116 of the conversation, causing the triage AI 111 to bring in AI specialist #1. After determining that the conversation has moved from topic #1 to topic #2, the triage AI 111 may remove AI specialist #1 and bring in AI specialist #2. Typically, a patient may have 3-5 complaints (symptoms). For example, assume the patient 120 has been in an automobile accident, in which the patient 120 has a concussion, a pneumothorax (a collapsed lung), and a fractured femur. Based on detecting the word "concussion" spoken by the doctor 118 in the conversation, the triage AI 111 brings in an AI neurologist (from the AI specialists 112) into the subset 146. Based on detecting the trigger word "pneumothorax" (or the set of trigger words "collapsed lung") spoken by the doctor 118 in the conversation, the triage AI 111 brings in an AI pulmonologist (from the AI specialists 112) into the subset 146. Based on detecting the trigger word "fracture" (or the set of trigger words "fractured <bone name>") spoken by the doctor 118 in the conversation, the triage AI 111 brings in an AI orthopedist (from the AI specialists 112) into the subset 146. The AI specialists 1002 in the subset 146 access the current portion of the conversation. Each AI specialist 1002 in the subset 146 independently determines treatment protocols, medications, lab work, and other details related to their specialty and provides an opinion 1006 and reasoning 1008 associated with the opinion 1006 that includes a diagnosis based on their specialty. For example, the AI specialist 1002(1) provides the opinion 1006(1) and associated reasoning 1008(1) and the AI specialist 1002(M) provides the opinion 1006(M) and associated reasoning 1008(M). The consensus AI 148 reviews the opinions 1006 and reasoning 1008, from each AI specialist 1002 in the subset 146 and determines a final diagnosis, the consensus answer 162 which is presented to the doctor 118 as one of the decision support insights.

After the triage AI 111 determines that the conversation between the doctor and the patient has ended, the consensus AI 148 receives the opinions 1006 from each AI specialist 1002 that was brought in to the subset 146 during the conversation and weights their opinions 1006. The reasoning 1008 may include several different types of reasoning, such as, for example, clinical reasoning, scientific reasoning, and elimination reasoning. Clinical reasoning is what an actual physician would do in an examination room. The physician thinks through the problem. What the physician does is based off of the presentation, what the set of symptoms are, what the patient is saying, what the lab results are, and so on, to come to the opinion 1006. Scientific reasoning is based off of literature, but also more off of the first few years of medical school, e.g., microbiology, pathology, histology, biochemistry, biochemical pathways for reactions, and so on. These are things that a physician learned in medical school but doesn't think about when in practice. The AI specialists 1002 use scientific reasoning because taking this type of information into account can be useful, particularly for edge cases. In some cases, the scientific reasoning may enhance the clinical reasoning. In elimination reasoning, each AI specialist thinks things through and eliminates what is highly unlikely based on each AI specialist's opinions 1006 and, in some cases, based off of reviewing the opinions 1006 of the subset 146 of AI specialists 1002 that were brought in. All of this occurs before the response AI 150 makes a final decision. The response AI 150 takes into account the opinions 1006 (and associated reasoning 1008) of the AI specialists 1002 and provides an output that included the consensus answer 162. Elimination reasoning may use adversarial testing and red-teaming to eliminate unlikely conclusions. Elimination reason may include adversarial reasoning and self-critique. Adversarial reasoning involves one AI specialist's output being critically evaluated by other AI specialists (included in the subset 146) to balance out biases and prevent overreliance on a single AI specialist's output. Self-critique means individual AI specialists actively identify weaknesses in their own reasoning.

In some cases, the AI specialists 1002 may work in isolation while in other cases the AI specialists 1002 may communicate with each other by asking questions, offering an opinion, or the like. At the end of the conversation between the doctor and the patient, each AI specialist 1002 that was included in the subset 146 provides their opinion 1006. After the AI specialists 1002 have each come up with their opinion 1006, the AI specialists 1002 may discuss their respective opinions 1006 amongst themselves and, in some cases, may alter their opinions 1006 based on the discussion.

The consensus AI 148 assimilates the opinions 1006 and the reasoning 1008 provided by the AI specialists 1002 in the subset 146. Each AI specialist 1002 is trained in their particular area of medicine. In contrast, the consensus AI 148 assimilates the opinions 1006 and the reasoning 1008 from the AI specialists 1002 and determines the consensus answer 162 that includes a final decision on the final diagnosis and a plan as to how to move forward, including prioritizing outputs 1010 from the AI specialists 1002. In the car accident example, the most important thing is pulmonology, because the collapsed lung, if not treated in a timely manner, will decompensate the patient. In this example, the outputs of the neurologist AI and the orthopedic AI are secondary to the output of the pulmonologist AI. In this way, the system 100 is able to provide decision support insights that reflect the output of multiple AI specialists, something that is not possible when using a single AI. Thus, the combination of the triage AI 111, the AI specialists 112, and the consensus AI 148 are able to provide the doctor 118 with a comprehensive plan that takes into account all of the patient's set of symptoms 166 (e.g., pneumothorax, broken femur, concussion) and prioritizes each symptom's treatment.

The triage AI 111 and/or the consensus AI 148 may generate questions MC 156 for the AI specialists 1002 and analyze output 1010 from the AI specialists 1002. The questions MC 156 may include multiple choice questions, binary response questions (response is either yes or no), one phrase response questions (what, in your opinion, is the most important diagnosis), or other types of questions. For example, the answers 158 may be used by the triage AI 111 to determine an order (from most serious to least serious) in which to analyze the set of symptoms of the patient. In this way, potentially life threatening symptoms (e.g., collapsed lung) may be dealt with before other symptoms.

The consensus AI 148 is trained on how clinicians actually practice medicine, meaning that it's trained on the transcripts of conversations that physicians have with patients and what the physician has decided to do based off of their conversation with the patient. The consensus AI 148 receives the outputs 1010 of all of the AI specialists 1002. The consensus AI 148 determines the major insights to provide the doctor 118 during their interaction with the patient 120, what questions the patient 120 should be asked and in what order, what protocols need to be assessed immediately, and so on.

After determining that the conversation has ended, the consensus AI 148 looks at the entire conversation, along with the opinions 1006 (including reasoning 1008 behind the opinions 1006) and prioritizes the needs of the patient accordingly. The consensus AI 148 assigns a weight 1004 to each specialist AI 1002 answers 158 based on the conversation. For example, if a person in a car accident has a broken rib and is having breathing issues, then the broken rib is the main focus initially (because it could cause the most damage if left untreated) and everything else is secondary. Thus, the consensus AI 148 makes a conclusion (consensus answer 162) at the end of the conversation in real time. The AI specialists 1002 provide opinions 1006 and provide reasoning 1008, which the consensus AI 148 uses to determine a final plan that includes the consensus answer 162. The consensus AI 148 makes the final decision, similar to an attending physician, at the end of the conversation. In straightforward cases, one AI specialist 1002 may be brought in to the subset 146 but for more complicated cases, multiple AI specialists 1002 may be brought in. Typically, in complicated cases, there may be 3 to 5 AI specialists in the subset 146, at any given point in time during the conversation. The multiple opinions 1006 from multiple AI specialists 1006 results in improved outcomes for patients.

After determining that the conversation has ended, each of the AI specialists 1002 that were brought in to the subset 146 may be asked multiple questions 156 by the consensus AI 148. Each AI specialist 1002 independently provides an answer 158 to each of the questions 156, and the consensus AI 148 selects an answer that is chosen by the majority as the consensus answer 162 that is provided to the doctor 118. In some cases, to further improve accuracy, each AI specialist 1002 may provide a confidence level 160 for each answer 158 and the consensus AI 148 may use the confidence level 160 to weight each of the answers 158. Each AI specialist 1002 provides the answer 158 to each multiple choice question 156 and provides an associated confidence level 160 for each answer. The answer 158 (to each multiple choice question 156) provided by one of the AI specialists 1002 is weighted based on the confidence level 160 associated with the answer 158. Thus, when an AI specialist 1002 expresses a higher confidence level 160 in a particular answer 158, the particular answer 158 is given more influence. The consensus AI 148 determines the consensus answer 162 based on a weighted score of the answers 158 and associated confidence level 160. Providing the confidence level 160 enables the AI specialists 1002 with strong predictions to influence the consensus answer 162. In some cases, the consensus agent 148 will first assess the question 156 and assign an additional weight 1004 to each AI specialist 1002 (that was brought into the subset 146) to further boost the confidence weighting. For example, for a question related to a particular specialty, the response of an AI specialist associated with the particular specialist may be given great weight than the answers of other AI specialists. To illustrate, for a question related to bones, the answer provided by the orthopedic AI specialist may be given greater weight than other AI specialists, for a question related to lungs/breathing, the answer provided by the pulmonologist AI specialist may be given greater weight than other AI specialists, for a question that is cardiovascular-related, the answer provided by the cardiologist AI specialist may be given greater weight than other AI specialists, and so on. The weighted score may be determined as follows (assuming M number of AI specialists, M>0):

Weighted score for an answer=SUM[((answer #1)×(confidence #1)×(AI specialist #1 weight))+ . . . ((answer #*M*)×(Confidence #*M*)×(AI Specialist #*M* Weight))

The example systems and computing devices described herein are merely examples suitable for some implementations and are not intended to suggest any limitation as to the scope of use or functionality of the environments, architectures and frameworks that can implement the processes, components and features described herein. Thus, implementations herein are operational with numerous environments or architectures, and may be implemented in general purpose and special-purpose computing systems, or other devices having processing capability. Generally, any of the functions described with reference to the figures can be implemented using software, hardware (e.g., fixed logic circuitry) or a combination of these implementations. The term "module," "mechanism" or "component" as used herein generally represents software, hardware, or a combination of software and hardware that can be configured to implement prescribed functions. For instance, in the case of a software implementation, the term "module," "mechanism" or "component" can represent program code (and/or declarative-type instructions) that performs specified tasks or operations when executed on a processing device or devices (e.g., CPUs or processors). The program code can be stored in one or more computer-readable memory devices or other computer storage devices. Thus, the processes, components and modules described herein may be implemented by a computer program product.

Furthermore, this disclosure provides various example implementations, as described and as illustrated in the drawings. However, this disclosure is not limited to the implementations described and illustrated herein, but can extend to other implementations, as would be known or as would become known to those skilled in the art. Reference in the specification to "one implementation," "this implementation," "these implementations" or "some implementations" means that a particular feature, structure, or characteristic described is included in at least one implementation, and the appearances of these phrases in various places in the specification are not necessarily all referring to the same implementation.

Although the present technology disclosed has been described in connection with several implementations, the technology disclosed is not intended to be limited to the specific forms set forth herein. On the contrary, it is intended to cover such alternatives, modifications, and equivalents as can be reasonably included within the scope of the technology disclosed as defined by the appended claims.

Some implementations of the technology disclosed relate to using a Transformer model to provide a multi-turn conversational system. In particular, the technology disclosed proposes a parallel input, parallel output (PIPO) multi-turn conversational system based on the Transformer architecture. The Transformer model relies on a self-attention mechanism to compute a series of context-informed vector-space representations of elements in the input sequence and the output sequence, which are then used to predict distributions over subsequent elements as the model predicts the output sequence element-by-element. Not only is this mechanism straightforward to parallelize, but as each input's representation is also directly informed by all other inputs' representations, this results in an effectively global receptive field across the whole input sequence. This stands in contrast to, e.g., convolutional architectures which typically only have a limited receptive field.

In one implementation, the disclosed multi-turn conversational system is a multilayer perceptron (MLP). In another implementation, the disclosed multi-turn conversational system is a feedforward neural network. In yet another implementation, the disclosed multi-turn conversational system is a fully connected neural network. In a further implementation, the disclosed multi-turn conversational system is a fully convolution neural network. In a yet further implementation, the disclosed multi-turn conversational system is a semantic segmentation neural network. In a yet another further implementation, the disclosed multi-turn conversational system is a generative adversarial network (GAN) (e.g., CycleGAN, StyleGAN, pixelRNN, text-2-image, DiscoGAN, IsGAN). In a yet another implementation, the disclosed multi-turn conversational system includes self-attention mechanisms like Transformer, Vision Transformer (ViT), Bidirectional Transformer (BERT), Detection Transformer (DETR), Deformable DETR, UP-DETR, DeiT, Swin, GPT, iGPT, GPT-2, GPT-3, various ChatGPT versions, various LLAMA versions, BERT, SpanBERT, ROBERTa, XLNet, ELECTRA, UniLM, BART, T5, ERNIE (THU), KnowBERT, DeiT-Ti, DeiT-S, DeiT-B, T2T-ViT-14, T2T-ViT-19, T2T-VIT-24, PVT-Small, PVT-Medium, PVT-Large, TNT-S, TNT-B, CPVT-S, CPVT-S-GAP, CPVT-B, Swin-T, Swin-S, Swin-B, Twins-SVT-S, Twins-SVT-B, Twins-SVT-L, Shuffle-T, Shuffle-S, Shuffle-B, XCiT-S12/16, CMT-S, CMT-B, VOLO-D1, VOLO-D2, VOLO-D3, VOLO-D4, MoCo v3, ACT, TSP, Max-DeepLab, VisTR, SETR, Hand-Transformer, HOT-Net, METRO, Image Transformer, Taming transformer, TransGAN, IPT, TTSR, STTN, Masked Transformer, CLIP, DALL-E, Cogview, UniT, ASH, TinyBert, FullyQT, ConvBert, FCOS, Faster R-CNN+FPN, DETR-DC5, TSP-FCOS, TSP-RCNN, ACT+MKDD (L=32), ACT+MKDD (L=16), SMCA, Efficient DETR, UP-DETR, UP-DETR, VITB/16-FRCNN, VIT-B/16-FRCNN, PVT-Small+RetinaNet, Swin-T+RetinaNet, Swin-T+ATSS, PVT-Small+DETR, TNT-S+DETR, YOLOS-Ti, YOLOS-S, and YOLOS-B.

In one implementation, the disclosed multi-turn conversational system is a convolution neural network (CNN) with a plurality of convolution layers. In another implementation, the disclosed multi-turn conversational system is a recurrent neural network (RNN) such as a long short-term memory network (LSTM), bi-directional LSTM (Bi-LSTM), or a gated recurrent unit (GRU). In yet another implementation, the disclosed multi-turn conversational system includes both a CNN and an RNN.

In yet other implementations, the disclosed multi-turn conversational system can use 1D convolutions, 2D convolutions, 3D convolutions, 4D convolutions, 5D convolutions, dilated or atrous convolutions, transpose convolutions, depthwise separable convolutions, pointwise convolutions, 1×1 convolutions, group convolutions, flattened convolutions, spatial and cross-channel convolutions, shuffled grouped convolutions, spatial separable convolutions, and deconvolutions. The disclosed multi-turn conversational system can use one or more loss functions such as logistic regression/log loss, multi-class cross-entropy/softmax loss, binary cross-entropy loss, mean-squared error loss, L1 loss, L2 loss, smooth L1 loss, and Huber loss. The disclosed multi-turn conversational system can use any parallelism, efficiency, and compression schemes such TFRecords, compressed encoding (e.g., PNG), sharding, parallel calls for map transformation, batching, prefetching, model parallelism, data parallelism, and synchronous/asynchronous stochastic gradient descent (SGD). The disclosed multi-turn conversational system can include upsampling layers, downsampling layers, recurrent connections, gates and gated memory units (like an LSTM or GRU), residual blocks, residual connections, highway connections, skip connections, peephole connections, activation functions (e.g., non-linear transformation functions like rectifying linear unit (ReLU), leaky ReLU, exponential liner unit (ELU), sigmoid and hyperbolic tangent (tanh)), batch normalization layers, regularization layers, dropout, pooling layers (e.g., max or average pooling), global average pooling layers, and attention mechanisms.

The disclosed multi-turn conversational system can be a linear regression model, a logistic regression model, an Elastic Net model, a support vector machine (SVM), a random forest (RF), a decision tree, and a boosted decision tree (e.g., XGBoost), or some other tree-based logic (e.g., metric trees, kd-trees, R-trees, universal B-trees, X-trees, ball trees, locality sensitive hashes, and inverted indexes). The disclosed multi-turn conversational system can be an ensemble of multiple models, in some implementations.

In some implementations, the disclosed multi-turn conversational system can be trained using backpropagation-based gradient update techniques. Example gradient descent techniques that can be used for training the disclosed multi-turn conversational system include stochastic gradient descent, batch gradient descent, and mini-batch gradient descent. Some examples of gradient descent optimization algorithms that can be used to train the disclosed multi-turn conversational system are Momentum, Nesterov accelerated gradient, Adagrad, Adadelta, RMSprop, Adam, AdaMax, Nadam, and AMSGrad.

Transformer Logic

Machine learning is the use and development of computer systems that can learn and adapt without following explicit instructions, by using algorithms and statistical models to analyze and draw inferences from patterns in data. Some of the state-of-the-art models use Transformers, a more powerful and faster model than neural networks alone. Transformers originate from the field of natural language processing (NLP), but can be used in computer vision and many other fields. Neural networks process input in series and weight relationships by distance in the series. Transformers can process input in parallel and do not necessarily weigh by distance. For example, in natural language processing, neural networks process a sentence from beginning to end with the weights of words close to each other being higher than those further apart. This leaves the end of the sentence very disconnected from the beginning causing an effect called the vanishing gradient problem. Transformers look at each word in parallel and determine weights for the relationships to each of the other words in the sentence. These relationships are called hidden states because they are later condensed for use into one vector called the context vector. Transformers can be used in addition to neural networks. This architecture is described here.

What is claimed is:

1. A system comprising:
one or more processors; and
one or more non-transitory computer-readable storage media to store instructions executable by the one or more processors to perform operations comprising:
continually receiving, by a triage artificial intelligence, a portion of a conversation between a doctor and a patient, the triage artificial intelligence comprising a large language model that has been trained using multiple audio conversations between doctors and patients;
based on determining, by the triage artificial intelligence, that the conversation includes a first set of trigger words associated with a first symptom of the patient, selecting, by the triage artificial intelligence and based on the first symptom a first artificial intelligence specialist in a first medical specialty from a plurality of artificial intelligence specialists;
providing the first artificial intelligence specialist with access to the conversation between the doctor and the patient;
based on determining, by the triage artificial intelligence, that the conversation includes a second set of trigger words associated with a second symptom of the patient, selecting, by the triage artificial intelligence and based on the second symptom, a second artificial intelligence specialist in a second medical specialty from the plurality of artificial intelligence specialists;
providing the second artificial intelligence specialist with access to the conversation between the doctor and the patient;
sending a set of questions to a subset of the plurality of artificial intelligence specialists, the subset including the first artificial intelligence specialist and the second artificial intelligence specialist;
assigning, by a consensus artificial intelligence and based on a particular symptom associated with individual questions in the set of questions, a specialist weight to individual specialists in the subset of the plurality of artificial intelligence specialists;
receiving a set of answers from the subset of the plurality of artificial intelligence specialists;
determining, by the consensus artificial intelligence, a consensus answer to the set of questions based at least in part on using the specialist weight on individual answers in the set of answers;
providing the consensus answer to a continually updated graphical user interface of a computing device associated with the doctor; and
retraining the triage artificial intelligence using at least the conversation between the doctor and the patient.

2. The system of claim 1, wherein medical specialties associated with the plurality of artificial intelligence specialists comprise:
cardiology, neurology, nephrology, endocrinology, pediatrics, geriatrics, emergency medicine, ear-nose-throat (ENT), urology, gynecology, orthopedics, gastroenterology, pulmonology, hematology, oncology, rheumatology, internal medicine, and immunology.

3. The system of claim 1, the operations further comprising:
receiving, by the consensus artificial intelligence and from the subset of the plurality of artificial intelligence specialists, a confidence level associated with individual answers from the set of answers; and
determining, by the consensus artificial intelligence, the consensus answer based at least in part on using the confidence level as an additional weight to weight individual answers from the set of answers.

4. The system of claim 1, wherein assigning, by the consensus artificial intelligence, the specialist weight to individual specialists in the subset of the plurality of artificial intelligence specialists comprises:

assigning, based on the first symptom, a first specialist weight to a first subset of answers, in the set of answers, received from the first artificial intelligence specialist; and assigning, based on the second symptom, a second specialist weight to a second subset of answers, in the set of answers, received from the second artificial intelligence specialist.

5. The system of claim 1, the operations further comprising:

accessing, by the first artificial intelligence specialist, current medical knowledge in one or more medical knowledge databases; and performing, by the first artificial intelligence specialist, retrieval augmented generation to create one or more decision support insights.

6. The system of claim 1, wherein individual artificial intelligence specialists in the plurality of artificial intelligence specialists are configured to use one or more chain of thought techniques comprising one or more of:

structured chain of thought that uses step-by-step diagnostic reasoning;

multi-perspective chain of thought that takes into consideration differential diagnoses from multiple angles;

self-critique chain of thought that involves identifying potential errors in the individual artificial intelligence specialists' own reasoning;

probabilistic chain of thought in which a confidence level is provided with each diagnostic hypothesis; or any combination thereof.

7. The system of claim 1, the operations further comprising:

based on determining, by the triage artificial intelligence, that the conversation is no longer discussing the first symptom, disabling access to the conversation between the doctor and the patient for the first artificial intelligence specialist.

8. A computer-implemented method comprising:

continually receiving, by a triage artificial intelligence, a portion of a conversation between a doctor and a patient, the triage artificial intelligence comprising a large language model that has been trained using training data that includes multiple audio conversations between doctors and patients;

based on determining, by the triage artificial intelligence, that the conversation includes a first set of trigger words associated with a first symptom of the patient, selecting, by the triage artificial intelligence and based on the first symptom, a first artificial intelligence specialist in a first medical specialty from a plurality of artificial intelligence specialists;

providing the first artificial intelligence specialist with access to the conversation between the doctor and the patient;

based on determining, by the triage artificial intelligence, that the conversation includes a second set of trigger words associated with a second symptom of the patient, selecting, by the triage artificial intelligence and based on the second symptom, a second artificial intelligence specialist in a second medical specialty from the plurality of artificial intelligence specialists;

providing the second artificial intelligence specialist with access to the conversation between the doctor and the patient;

sending a set of questions to a subset of the plurality of artificial intelligence specialists, the subset including the first artificial intelligence specialist and the second artificial intelligence specialist;

assigning, by a consensus artificial intelligence and based on a particular symptom associated with individual questions in the set of questions, a specialist weight to individual specialists in the subset of the plurality of artificial intelligence specialists;

receiving a set of answers from the subset of the plurality of artificial intelligence specialists;

determining, by the consensus artificial intelligence, a consensus answer to the set of questions based at least in part on using the specialist weight on individual answers in the set of answers;

providing the consensus answer to a continually updated graphical user interface of a computing device associated with the doctor; and retraining the triage artificial intelligence using at least the conversation between the doctor and the patient.

9. The computer-implemented method of claim 8, wherein individual artificial intelligence specialists in the plurality of artificial intelligence specialists are configured to use chain of thought techniques comprising one or more of:

structured chain of thought that uses step-by-step diagnostic reasoning;

multi-perspective chain of thought that takes into consideration differential diagnoses from multiple angles;

self-critique chain of thought that involves identifying potential errors in the individual artificial intelligence specialists' own reasoning;

probabilistic chain of thought in which a confidence level is provided with each diagnostic hypothesis; or any combination thereof.

10. The computer-implemented method of claim 8, further comprising:

receiving, by the consensus artificial intelligence and from the subset of the plurality of artificial intelligence specialists with access to the conversation between the doctor and the patient, a confidence level associated with individual answers from the set of answers; and determining, by the consensus artificial intelligence, the consensus answer to individual questions in the set of questions based at least in part on using the confidence level to weight individual answers from the set of answers.

11. The computer-implemented method of claim 8, further comprising:

accessing, by the second artificial intelligence specialist, current medical knowledge in one or more medical knowledge databases;

performing, by the second artificial intelligence specialist, retrieval augmented generation to create one or more decision support insights; and presenting the one or more decision support insights to the continually updated graphical user interface of the computing device associated with the doctor.

12. The computer-implemented method of claim 8, further comprising:

based on determining, by the triage artificial intelligence, that the conversation is no longer discussing the second symptom, disabling access to the conversation between the doctor and the patient for the second artificial intelligence specialist.

13. The computer-implemented method of claim 8, wherein medical specialties associated with the plurality of artificial intelligence specialists comprise:

cardiology, neurology, nephrology, endocrinology, pediatrics, geriatrics, emergency medicine, ear-nose-throat (ENT), urology, gynecology, orthopedics, gastroenterology, pulmonology, hematology, oncology, rheumatology, internal medicine, and immunology.

14. The computer-implemented method of claim 8, wherein individual artificial intelligence specialists in the plurality of artificial intelligence specialists are configured to use one or more of:

clinical reasoning by performing a patient-centered analysis based on symptoms, clinical presentation, and standard medical practices;

scientific reasoning by performing a mechanism-based analysis based on pathophysiology, biochemistry, and scientific foundations;

elimination reasoning using an adversarial testing protocol in which edge cases are tested and bias detection is performed for demographic bias and presentation bias; or any combination thereof.

15. One or more non-transitory computer-readable storage media to store instructions executable by one or more processors to perform operations comprising:

continually receiving, by a triage artificial intelligence, a portion of a conversation between a doctor and a patient, the triage artificial intelligence comprising a large language model that has been trained using multiple audio conversations between doctors and patients;

based on determining, by the triage artificial intelligence, that the conversation includes a first set of trigger words associated with a first symptom of the patient, selecting, by the triage artificial intelligence and based on the first symptom, a first artificial intelligence specialist in a first medical specialty from a plurality of artificial intelligence specialists;

providing the first artificial intelligence specialist with access to the conversation between the doctor and the patient;

based on determining, by the triage artificial intelligence, that the conversation includes a second set of trigger words associated with a second symptom of the patient, selecting, by the triage artificial intelligence and based on the second symptom, a second artificial intelligence specialist in a second medical specialty from the plurality of artificial intelligence specialists;

providing the second artificial intelligence specialist with access to the conversation between the doctor and the patient;

sending a set of questions to a subset of the plurality of artificial intelligence specialists, the subset including the first artificial intelligence specialist and the second artificial intelligence specialist;

assigning, by a consensus artificial intelligence and based on a particular symptom associated with individual questions in the set of questions, a specialist weight to individual specialists in the subset of the plurality of artificial intelligence specialists;

receiving a set of answers from the subset of the plurality of artificial intelligence specialists;

determining, by the consensus artificial intelligence, a consensus answer to the set of questions based at least in part on using the specialist weight on individual answers in the set of answers;

providing the consensus answer to a continually updated graphical user interface of a computing device associated with the doctor; and retraining the triage artificial intelligence using at least the conversation between the doctor and the patient.

16. The one or more non-transitory computer-readable storage media of claim 15, wherein assigning, by the consensus artificial intelligence, the specialist weight to individual specialists in the subset of the plurality of artificial intelligence specialists comprises:

assigning, based on the first symptom, a first specialist weight to a first subset of answers, in the set of answers, received from the first artificial intelligence specialist; and assigning, based on the second symptom, a second specialist weight to a second subset of answers, in the set of answers, received from the second artificial intelligence specialist.

17. The one or more non-transitory computer-readable storage media of claim 15, the operations further comprising:

receiving, by the consensus artificial intelligence and from the subset of the plurality of artificial intelligence specialists with access to the conversation between the doctor and the patient, a confidence level associated with individual answers from the set of answers; and determining, by the consensus artificial intelligence, the consensus answer to individual questions in the set of questions based at least in part on using the confidence level to weight individual answers from the set of answers.

18. The one or more non-transitory computer-readable storage media of claim 15, wherein medical specialties associated with the plurality of artificial intelligence specialists comprise:

cardiology, neurology, nephrology, endocrinology, pediatrics, geriatrics, emergency medicine, ear-nose-throat (ENT), urology, gynecology, orthopedics, gastroenterology, pulmonology, hematology, oncology, rheumatology, internal medicine, and immunology.

19. The one or more non-transitory computer-readable storage media of claim 15, wherein individual artificial intelligence specialists in the plurality of artificial intelligence specialists are configured to use one or more of:

clinical reasoning by performing a patient-centered analysis based on symptoms, clinical presentation, and standard medical practices;

scientific reasoning by performing a mechanism-based analysis based on pathophysiology, biochemistry, and scientific foundations;

elimination reasoning using an adversarial testing protocol in which edge cases are tested and bias detection is performed for demographic bias and presentation bias; or any combination thereof.

20. The one or more non-transitory computer-readable storage media of claim 15, the operations further comprising:

accessing, by the first artificial intelligence specialist, current medical knowledge in one or more medical knowledge databases; and performing, by the first artificial intelligence specialist, retrieval augmented generation to create one or more decision support insights.

* * * * *